US010239918B2

(12) United States Patent
Sherman et al.

(10) Patent No.: US 10,239,918 B2
(45) Date of Patent: Mar. 26, 2019

(54) CAHUITAMYCINS AND METHODS OF MAKING AND USING THE SAME

(71) Applicant: THE REGENTS OF THE UNIVERSITY OF MICHIGAN, Ann Arbor, MI (US)

(72) Inventors: David H. Sherman, Ann Arbor, MI (US); Fengan Yu, Ann Arbor, MI (US); Chuanwu Xi, Ann Arbor, MI (US); Jianfeng Wu, Ann Arbor, MI (US); Pamela J. Schultz, Superior Township, MI (US); Ashootosh Tripathi, Ypsilanti, MI (US); Sung Ryeol Park, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/576,494

(22) PCT Filed: May 26, 2016

(86) PCT No.: PCT/US2016/034216
§ 371 (c)(1),
(2) Date: Nov. 22, 2017

(87) PCT Pub. No.: WO2016/191514
PCT Pub. Date: Dec. 1, 2016

(65) Prior Publication Data
US 2018/0162906 A1    Jun. 14, 2018

Related U.S. Application Data

(60) Provisional application No. 62/166,786, filed on May 27, 2015.

(51) Int. Cl.
| | | |
|---|---|---|
| *C07K 4/00* | (2006.01) |
| *C07K 7/06* | (2006.01) |
| *A01N 37/46* | (2006.01) |
| *A01N 43/76* | (2006.01) |
| *C07K 5/00* | (2006.01) |
| *C07K 5/083* | (2006.01) |
| *C07K 5/103* | (2006.01) |
| *C07D 413/12* | (2006.01) |
| *A61K 38/07* | (2006.01) |
| *A61K 45/06* | (2006.01) |
| *C07K 14/195* | (2006.01) |
| *C12N 9/88* | (2006.01) |

(52) U.S. Cl.
CPC ............ *C07K 7/06* (2013.01); *A01N 37/46* (2013.01); *A01N 43/76* (2013.01); *A61K 38/07* (2013.01); *A61K 45/06* (2013.01); *C07D 413/12* (2013.01); *C07K 5/00* (2013.01); *C07K 5/081* (2013.01); *C07K 5/1013* (2013.01); *C07K 14/195* (2013.01); *C12N 9/88* (2013.01); *C12Y 402/99021* (2013.01)

(58) Field of Classification Search
None
See application file for complete search history.

(56) References Cited

U.S. PATENT DOCUMENTS

2008/0085866 A1    4/2008  Greenberg et al.

OTHER PUBLICATIONS

Sayedsayamdost, JACS, 2011, 133, 11434-11437 (Year: 2011).*
Abergel et al., Petrobactin-mediated iron transport in pathogenic bacteria: coordination chemistry of an unusual 3,4-catecholate/citrate siderophore, J. Am. Chem. Soc., 130(7):2124-5 (2008).
Altschul et al., Basic local alignment search tool, J. Mol. Biol., 215(3):403-10 (1990).
Andersson et al., Persistence of antibiotic resistance in bacterial populations, FEMS Microbiol. Rev., 35(5):901-11 (2011).
Bachmann et al., Chapter 8. Methods for in silico prediction of microbial polyketide and nonribosomal peptide biosynthetic pathways from DNA sequence data, Methods Enzymol., 458:181-217 (2009).
Bevan et al., Amino-acids and peptides. Part X. Characterisation of the monamycins, members of a new family of cyclodepsipeptide antibiotics , J. Chem. Soc. C: Organics, pp. 514-522 (1971).
Blin et al., antiSMASH 2.0—a versatile platform for genome mining of secondary metabolite producers, Nucleic Acids Res., 41(Web Server issue):W204-12 (2013).
Broberg et al., Kutznerides 1-4, depsipeptides from the actinomycete *Kutzneria* sp. 744 inhabiting mycorrhizal roots of *Picea abies* seedlings, J. Nat. Prod., 69(1):97-102 (2006).
Chang et al., In vitro activities of antimicrobial agents, alone and in combination, against Acinetobacter baumannii isolated from blood, Diagn. Microbiol. Infect. Dis., 23(3):105-10 (1995).
Chen et al., Gobichelin A and B: Mixed-Ligand Siderophores Discovered Using Proteomics, Medchemcomm., 4(1):233-8 (2013).
Cruz et al., Titration-based screening for evaluation of natural product extracts: identification of an aspulvinone family of luciferase inhibitors, Chem. Biol., 18(11):1442-52 (2011).
Daum et al., Organisation of the biosynthetic gene cluster and tailoring enzymes in the biosynthesis of the tetracyclic quinone glycoside antibiotic polyketomycin, Chembiochem., 10(6):1073-83 (2009).
Davies, Understanding biofilm resistance to antibacterial agents, Nat. Rev. Drug Discov., 2(2):114-22 (2003).

(Continued)

*Primary Examiner* — Satyanarayana R Gudibande
(74) *Attorney, Agent, or Firm* — Marshall, Gerstein & Borun LLP

(57) ABSTRACT

Provided herein are biofilm inhibitors obtained from marine microbial derived natural product extracts from *Streptomyces gandocaensis*, resulting in biofilm inhibitors, cahuitamycins. Also provided are mutant *S. gandocaensis*, methods of inhibiting biofilm formation, methods of producing, or increasing the production of, cahuitamycins, methods for synthesizing cahuitamycins, and methods of purifying cahuitamycins.

20 Claims, 4 Drawing Sheets
Specification includes a Sequence Listing.

(56) References Cited

OTHER PUBLICATIONS

Dijkshoorn et al., An increasing threat in hospitals: multidrug-resistant Acinetobacter baumannii, Nat. Rev. Microbiol., 5(12):939-51 (2007).
Fehr et al., Sanglifehrins A, B, C and D, novel cyclophilin-binding compounds isolated from *Streptomyces* sp. A92-308110. II. Structure elucidation, stereochemistry and physico-chemical properties, J. Antibiot (Tokyo), 52(5):474-9 (1999).
Feng et al., Progressive sequence alignment as a prerequisite to correct phylogenetic trees, J. Mol. Evol., 25(4):351-60 (1987).
Fischbach et al., Antibiotics for emerging pathogens, Science, 325(5944):1089-93 (2009).
Fujii et al., A Nonempirical Method Using LC/MS for Determination of the Absolute Configuration of Constituent Amino Acids in a Peptide:? Elucidation of Limitations of Marfey's Method and of Its Separation Mechanism, Anal. Chem., 69(16):3346-52 (1997).
Gaisser et al., Cloning of an avilamycin biosynthetic gene cluster from Streptomyces viridochromogenes Tü57, J. Bacteriol., 179(20):6271-8 (1997).
Harrison et al., The structure of MbtI from *Mycobacterium tuberculosis*, the first enzyme in the biosynthesis of the siderophore mycobactin, reveals it to be a salicylate synthase, J. Bacteriol., 188(17):6081-91 (2006).
Henikoff et al., Amino acid substitution matrices from protein blocks, Proc. Natl. Acad. Sci. USA, 89(22):10915-9 (1992).
Herbst et al., Structural basis of the interaction of MbtH-like proteins, putative regulators of nonribosomal peptide biosynthesis, with adenylating enzymes, J. Biol. Chem., 288(3):1991-2003 (2013).
Higgins et al., Fast and sensitive multiple sequence alignments on a microcomputer, Comput. Appl. Biosci., 5(2):151-3 (1989).
International Application No. PCT/US16/34216, International Preliminary Report on Patentability, dated Nov. 28, 2017.
International Application No. PCT/US16/34216, International Search Report and Written Opinion, dated Sep. 2, 2016.
Karlin et al., Applications and statistics for multiple high-scoring segments in molecular sequences, Proc. Natl. Acad. Sci. USA, 90(12):5873-7 (1993).
Lautru et al., Discovery of a new peptide natural product by Streptomyces coelicolor genome mining, Nat. Chem. Biol., 1(5):265-9 (2005).
Ling et al., Enediyne antitumor antibiotic maduropeptin biosynthesis featuring a C-methyltransferase that acts on a CoA-tethered aromatic substrate, J. Am. Chem. Soc., 132(36):12534-6 (2010).
Livermore et al., Discovery research: the scientific challenge of finding new antibiotics, J. Antimicrob. Chemother., 66(9):1941-4 (2011).
Magarvey et al., Isolation and characterization of novel marine-derived actinomycete taxa rich in bioactive metabolites, Appl. Environ. Microbiol., 70(12):7520-9 (2004).
Marahiel et al., Modular Peptide Synthetases Involved in Nonribosomal Peptide Synthesis, Chem. Rev., 97(7):2651-74 (1997).
Marfey, Determination ofD-amino acids. II. Use of a bifunctional reagent, 1,5-difluoro-2,4-dinitrobenzene, Carlsberg Res. Commun., 49:591 (1984).
Montaser et al., Marine natural products: a new wave of drugs?, Future Med. Chem., 3(12):1475-89 (2011).
Needleman et al., A general method applicable to the search for similarities in the amino acid sequence of two proteins, J. Mol. Biol., 48(3):443-53 (1970).
Neumann et al., Biosynthesis of piperazic acid via N5-hydroxy-ornithine in *Kutzneria* spp. 744, Chembiochem., 13(7):972-6 (2012).
Newman et al., Natural products as sources of new drugs over the 30 years from 1981 to 2010, J. Nat. Prod., 75(3):311-35 (2012).
Ochi et al., Ribosome engineering and secondary metabolite production, Adv. Appl. Microbiol., 56:155-84 (2004).
Park et al., Discovery of cahuitamycins as biofilm inhibitors derived from a convergent biosynthetic pathway, Nat. Commun., 7:10710 (2016).
Pearson et al., Improved tools for biological sequence comparison, Proc. Natl. Acad. Sci. USA, 85(8):2444-8 (1988).
Rainey et al., The genus *Nocardiopsis* represents a phylogenetically coherent taxon and a distinct actinomycete lineage: proposal of Nocardiopsaceae fam. nov, Int. J. Syst. Bacteriol., 46(4):1088-92 (1996).
Rao et al., Correlation between biofilm production and multiple drug resistance in imipenem resistant clinical isolates of Acinetobacter baumannii, Indian J. Med. Microbiol., 26(4):333-7 (2008).
Schneiker et al., Complete genome sequence of the myxobacterium Sorangium cellulosum, Nat. Biotechnol., 25(11):1281-9 (2007).
Seyedsayamdost et al., Structure and biosynthesis of amychelin, an unusual mixed-ligand siderophore from *Amycolatopsis* sp. AA4, J. Am. Chem. Soc., 133(30):11434-7 (2011).
Shao et al., Cloning and characterization of a bacterial iterative type I polyketide synthase gene encoding the 6-methylsalicyclic acid synthase, Biochem. Biophys. Res. Commun., 345(1):133-9 (2006).
Smith et al., Comparison of biosequences, Adv. Appl. Math., 2(4):482-9 (1981).
Sontag et al., Oxachelin, a novel iron chelator and antifungal agent from *Streptomyces* sp. GW9/1258, J. Antibiot. (Tokyo), 59(10):659-63 (2006).
Sunenshine et al., Multidrug-resistant Acinetobacter infection mortality rate and length of hospitalization, Emerg. Infect. Dis., 1391):97-103 (2007).
Tao et al., Valanimycin biosynthesis: investigations of the mechanism of isobutylhydroxylamine incorporation, Org. Lett., 5(8):1213-5 (2003).
Thompson et al., CLUSTAL W: improving the sensitivity of progressive multiple sequence alignment through sequence weighting, position-specific gap penalties and weight matrix choice, Nucleic Acids Res., 22(22):4673-80 (1994).
Umezawa et al., Biosynthesis of polyoxypeptin A: novel amino acid 3-hydroxy-3-methylproline derived from isoleucine, J. Chem. Soc. Perkin Trans. I, 1550-3 (2001).
Umezawa et al., Polyoxypeptins A and B Produced by Streptomyces: Apoptosis-Inducing Cyclic Depsipeptides Containing the Novel Amino Acid (2S,3R)-3-Hydroxy-3-methylproline, J. Org. Chem., 64(9):3034-8 (1999).
von Döhren et al., Multifunctional Peptide Synthetases, Chem. Rev., 97(7):2675-706 (1997).
Zhao et al., Complete genome sequence of the rifamycin SV-producing Amycolatopsis mediterranei U32 revealed its genetic characteristics in phylogeny and metabolism, Cell Res., 20(10):1096-108 (2010).
Zwahlen et al., Structure and mechanism of MbtI, the salicylate synthase from *Mycobacterium tuberculosis*, Biochemistry, 46(4):954-64 (2007).

\* cited by examiner

CAHUITAMYCINS AND METHODS OF MAKING AND USING THE SAME

CROSS-REFERENCE TO RELATED APPLICATION

The benefit under 35 U.S.C. 119(3) of U.S. Provisional Patent Application Ser. No. 62/166,786 filed May 27, 2015, is hereby claimed, and the disclosure thereof is hereby incorporated by reference herein.

STATEMENT OF GOVERNMENT SUPPORT

This invention was made with government support under TW007404 and AI057153 awarded by the National Institutes of Health. The government has certain rights in the invention.

BACKGROUND

Widespread antibiotic resistance is currently posing a grave health burden through a multitude of serious infections.[2] The rise in bacterial adaptation can be directly correlated to the paucity of novel classes of antimicrobial agents.[3] In the past few decades, synthetic tailoring has been the primary strategy for enhancing established core scaffolds through analog generation. Although this approach has been fruitful, no major classes of new antibiotics were introduced between 1962 and 2000.[4] Therefore, to restore robust access to effective therapeutic agents, it is imperative that we engage in aggressive efforts to discover novel chemical entities with unique microbial targets.[3,5]

Acinetobacter baumannii has emerged as a major nosocomial opportunistic pathogen that can spread epidemically among patients causing ventilator associated pneumonia and bacteremia, with mortality rates as high as 60%.[6] Numerous reports have also shown startling emergence of multidrug resistant A. baumannii in hospitals, and also identification of pandrug resistance strains at some locations.[1,6] A. baumanni strains possess both intrinsic resistance to antibiotics and a facile ability to acquire genes encoding resistance determinants. In addition, antibiotic resistance of this pathogenic microbe appears to be mediated by their facile ability to form biofilms with a highly structured extracellular polymeric matrix, and includes the ability to colonize medical devices.[7] When attached, bacterial cells that comprise the biofilm possess 10-1000 fold lower susceptibility towards antimicrobial agents compared to planktonic forms.[8] Although biofilm control by drug targeting has become a high priority objective,[7,8] marine microbes as a source of novel chemical entities remain underexplored.

SUMMARY

Provided herein are cahuitamycin compounds, compositions of cahuitamycin compounds, methods of using cahuitamycins, and methods of making or isolating cahuitamycins. In particular, provided herein are cahuitamycin compounds A, B, C, D, and E. Further provided are compositions comprising cahuitamycin A, B, C, D, or E with a pharmaceutically acceptable carrier.

Also provided are methods of inhibiting biofilm formation comprising contacting a bacterium capable for forming a biofilm with a compound or a composition as disclosed herein in an amount sufficient to inhibit the biofilm formation. The bacterium can be Acinetobacter baumannii, Aeromonas hydrophila, Aeromonas salmonicida, Agrobacterium tumefaciens, Brucella melitensis, Burkholderia cenocepacia, Burkholderia mallei, Burkholderia pseudomallei, Burkholderia vietnamiensis, Chromobacterium violaceum, Enterobacter agglomeran, Erwinia carotovora, Erwinia chrysanthemi, Escherichia coli, Nitrosomas europaea, Obesumbacterium proteus, Pantoea agglomerans, Pantoea stewartii, Pseudomonas aureofaciens, Pseudomonas aeruginosa, Pseudomonas fluorescens, Pseudomonas fuscovaginae, Pseudomonas syringae, Ralstonia solanacearum, Rhizobium etli, Rhizobium leguminosarum, Rhodobacter sphaeroides, Serratia liquefaciens, Serratia marcescens, Vibrio anguillarum, Vibrio fischeri, Vibrio parahaemolyticus, Vibrio salmonicida, Xanthomonas campestris, Xenorhabdus nematophilus, Yersinia enterocolitica, Yersinia pestis, Yersinia pseudotuberculosis, Yersinia medievalis, Yersinia ruckeri, or a combination thereof. In some cases, the bacterium is A. baumannii. The contacting can be in vitro or in vivo.

Further provided are methods of treating a condition due to biofilm formation in a subject in need thereof comprising administering a compound or composition as disclosed herein to the subject. The condition can be cystic fibrosis, dental caries, periodontis, otitis media, a muscular skeletal infection, pneumonia, necrotizing fasciitis, biliary tract infection, osteomyelitis, bacterial prostatitis, endocarditis, native valve endocarditis, cystic fibrosis pneumonia, meloidosis, a skin lesion associated with bullous impetigo, atopic dermatitis, pemphigus foliaceus, or an implanted device-related infection. Further contemplated is administration of a second therapeutic agent, such as an antibiotic.

Also provided herein is a mutant Streptomyces gandocaensis lacking salicylate synthase activity. In some cases, the mutant is DHS 334.

Further provided are methods of producing a cahuitamycin compound comprising culturing Streptomyces gandocaensis in the presence of streptomycin to select for a mutated ribosomal protein, thereby generating a mutated S. gandocaensis; and obtaining a cahuitamycin compound from the culture of mutated S. gandocaensis. In some cases, the rpsL gene is mutated.

Also provided herein are methods of producing a cahuitamycin compound comprising culturing Streptomyces gandocaensis under conditions wherein the activity of salicylate synthase is inhibited; and obtaining the cahuitamycin compound from the culture. In some cases, the methods further comprise a mutated ribosomal protein. In various cases, the Streptomyces gandocaensis comprises a cahI⁻ mutation. In some cases, the cahI⁻ mutation is a partial deletion of cahI. In some cases, the cahuitamycin compound obtained is cahuitamycin D or E, or a mixture thereof.

Further provided herein are methods of increasing the production of cahuitamycin A, cahuitamycin B, or a mixture of cahuitamycin A and B comprising culturing Streptomyces gandocaensis under conditions wherein the activity of 6-methylsalicylic acid synthase is inhibited; and obtaining the cahuitamycin compound from the culture.

Also provided herein are methods of synthesizing cahuitamycin D or E comprising culturing a Streptomyces gandocaensis mutant as described herein in the presence of 2-hydroxy-5-methylbenzoic acid or 2-hydroxybenzoic acid; and obtaining cahuitamycin D or E. In some cases, the method comprises culturing the Streptomyces gandocaensis mutant in the presence of 2-hydroxy-5-methylbenzoic acid to form cahuitamycin D. In various cases, the method comprises culturing the Streptomyces gandocaensis mutant in the presence of 2-hydroxy-benzoic acid to form cahuitamycin E. The method can further comprise isolating the cahuitamycin D or E. The isolating can be via extraction, chromatography or both. The extraction can be via contacting with an adsorbent resin, such as a styrene-divinylbenzene matrix. The chromatography can be one or more of fractionation, high performance liquid chromatography, and reverse phase liquid chromatography.

Further disclosed herein are methods comprising subjecting an extract from *Streptomyces gandocaensis* to extraction, chromatography, or both to isolate cahuitamycin A, B, or C. The extraction can be via contacting with an adsorbent resin, such as a styrene-divinylbenzene matrix. The chromatography can be one or more of fractionation, high performance liquid chromatography, and reverse phase liquid chromatography.

BRIEF DESCRIPTION OF THE DRAWINGS

FIG. 1A shows the sequence of rpsL gene (SEQ ID NO:1) from parent strain of *Streptomyces* sp. 12620-H2.

FIG. 1B shows the locations of rpsL gene mutations and resulting amino acid changes in *S.* sp. 12620-H2 (SEQ ID NOs: 1 and 2).

DETAILED DESCRIPTION

Figure 2A:
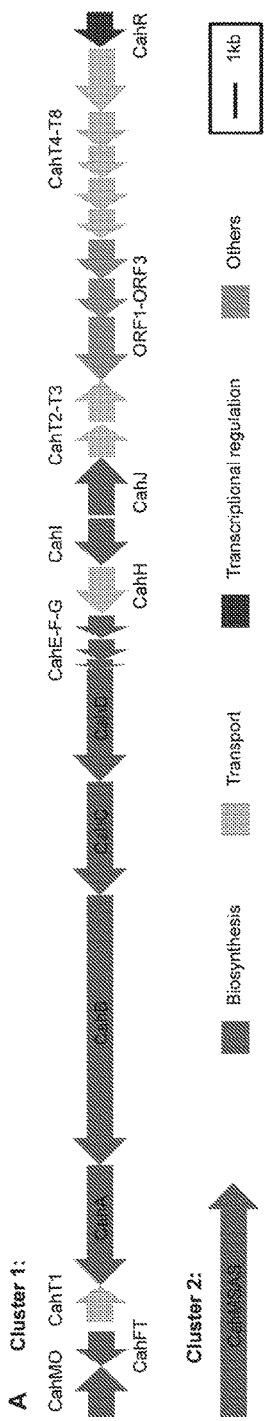
FIG. 2 shows the organization of the bifurcated cahuitamycin gene cluster (A) and a proposed biosynthetic pathway of cahuitamycins (B). Domain notation: T, thiolation; Cy, cyclization; A, adenylation; C, condensation; E, epimerization; CahMSAS, cahuitamycin 6-methylsaliciylic acid synthase.

In continuing effort to identify new structural classes of antibiotics,[5] static and flow based high-throughput assays were used to survey our natural product extract (NPE) library in the search for new inhibitors of biofilm formation.[9] Described herein is the discovery of three novel molecules, whose stable production and full structural identification required ribosomal engineering, and was facilitated by biosynthetic gene cluster characterization. In addition, shown herein is that the cahuitamycins are derived from two independent starter unit pathways, one of which is genetically unlinked to the core cluster. The bifurcated pathway allowed for directed pathway engineering to generate a new synthetic compound that was a potent molecule, selectively. Furthermore, mutasynthetic efforts on the ribosomally modulated strain generated two additional novel compounds with enhanced antibiotic activity.

In an effort to discover new antibiotics, a marine microbial-derived NPE library was screened to identify biofilm inhibitors in *A. baumannii*. Natural products accounts for the majority of currently marketed drugs,[10] and the marine environment represents a potential new source of unique chemical entities.[11] A crystal violet based high throughput assay was used to query against a library of 9,831 marine microbial derived NPEs in order to identify the extracts inhibiting biofilm formation as primary screen. The active extracts obtained in primary high-throughput screening were further prioritized by setting the inhibition threshold to 50% followed by a dose response assay, yielding 31 active NPEs. A second round of microbial biological activity analysis was conducted on the top nine most potent extracts. This study revealed *Streptomyces gandocaensis* to be of particular interest due to its ability to inhibit biofilm formation, but showing a limited effect on *A. baumannii* growth.

Figures 1A, 1B:
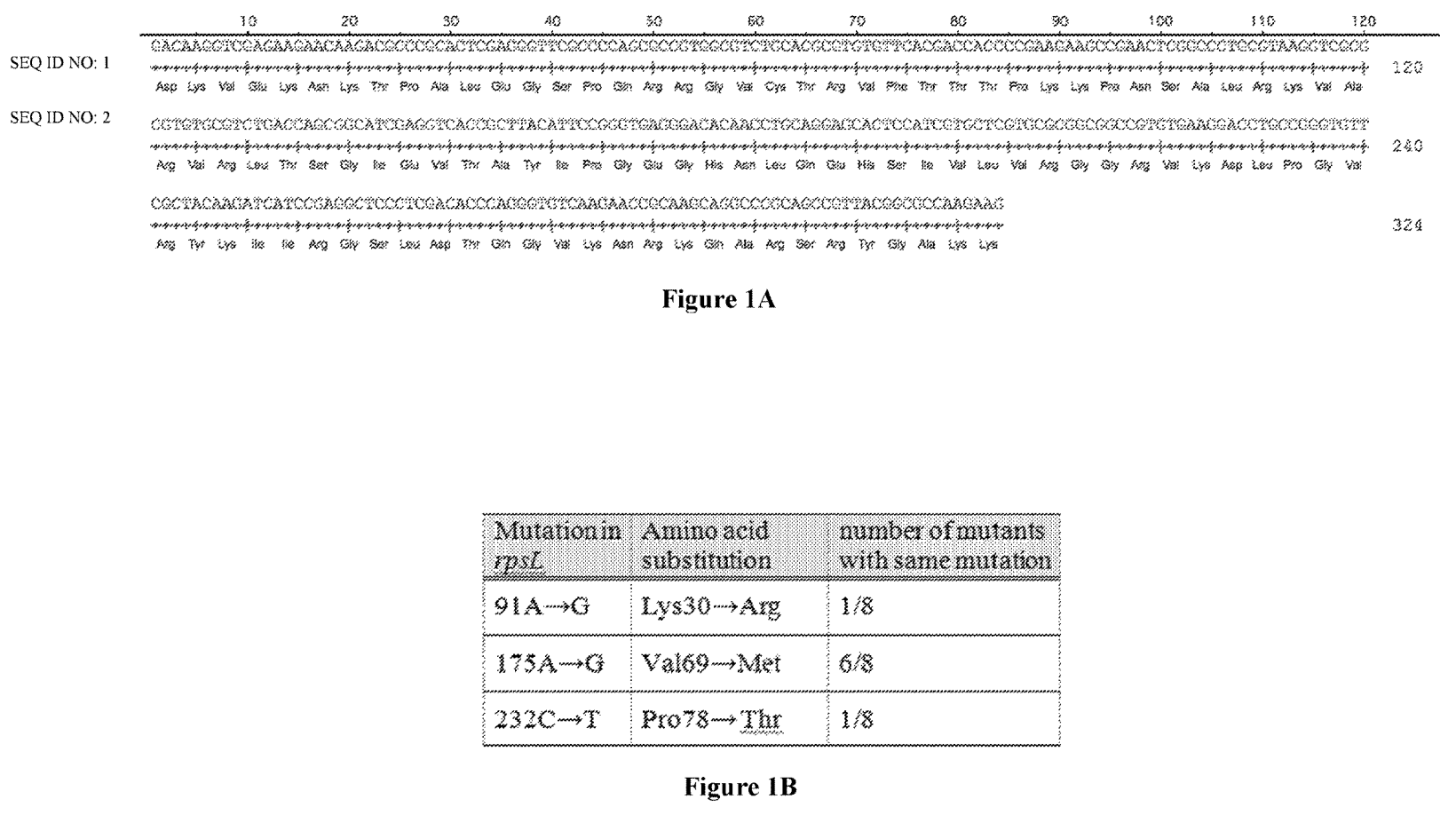

Due to the decreasing and then complete loss of production of the active biofilm inhibitor molecules from wild type *S. gandocaensis*, a ribosome engineering approach was employed to stabilize and improve production of the active metabolite. The approach has been employed for activation of secondary metabolite production in *Streptomyces* sp.,[12] and can result in enhanced yields by inducing point mutation in ribosomal protein-encoding genes (e.g. rpsL). Several rounds of mutagenesis based on a streptomycin resistance phenotype resulted in restored production and an improved strain DHS287 of *S. gandocaensis*, that generates several-fold increased quantities of active molecules compared to initial wild type levels. Genetic analysis of the mutated strain revealed that the streptomycin-induced ribosome engineering introduced a point mutation in the rpsL gene, which encodes the ribosomal protein S12, in the engineered strain (FIGS. 1A and 1B).

Previous studies have shown that mutations in the S12 gene renders cells potentially more active for polypeptide synthesis under typical starvation conditions during the late growth phase.[12] This effort appears to be the first reported instance where complete loss of an active, but structurally uncharacterized natural product has been recovered using the ribosomal engineering approach.

Isolation and Structure Elucidation of Cahuitamycins (1-3)

Bioassay guided C18 column fractionation followed by HPLC purification of organic extracts obtained from the ribosome engineered *S. gandocaensis* DHS287 yielded three new molecules, cahuitamycins A-C(1-3).

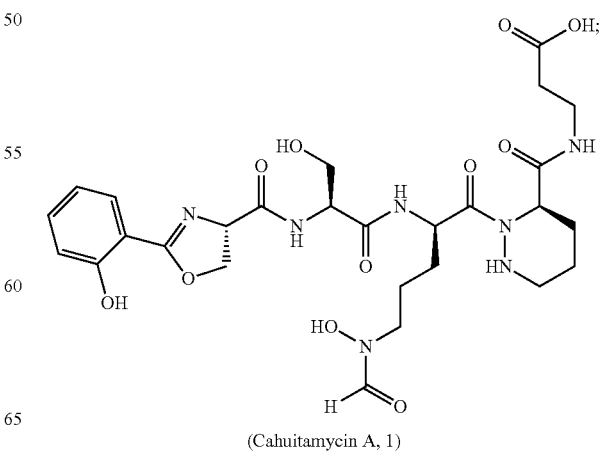

(Cahuitamycin A, 1)

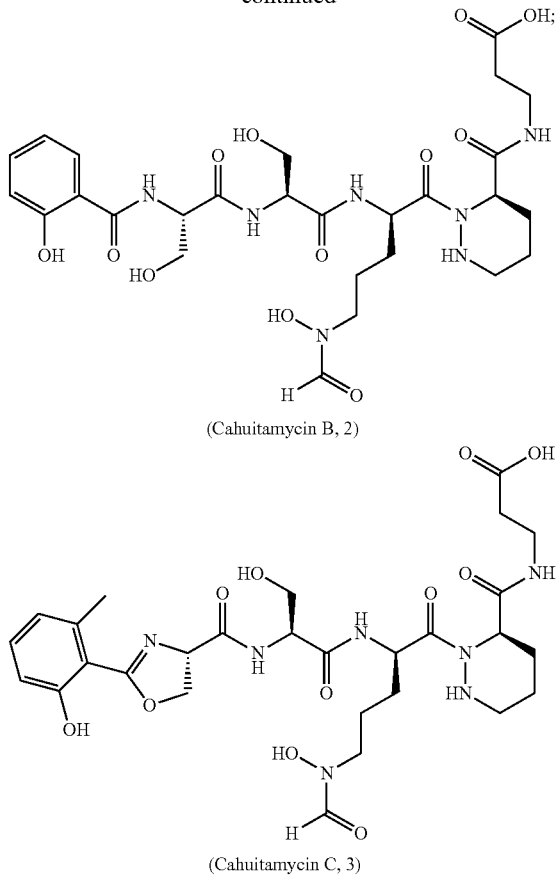

(Cahuitamycin B, 2)

(Cahuitamycin C, 3)

Cahuitamycin A (1), the major metabolite, showed a high resolution TOF-ESIMS [M+H]$^+$ ion peak at m/z 636.2679, indicating the molecular formula of $C_{27}H_{37}N_7O_{11}$ (+0.3 ppm) requiring 13 degree of unsaturation. The 1D ($^1$H, $^{13}$C) and 2D (gHSQCAD, gHMBCAD, gCOSY) NMR data acquired in $CD_3OD+D_2O$ (4:1) indicated the peptidic nature of 1 by the presence of 8 methyl/methine carbons, 10 methylene carbons, and 9 carbonyls/quaternary carbons. Analysis of gCOSY, TOCSY and gHMBC cross peaks at $\delta_H$ 7.01, 7.48, 6.97 and 7.71 to $\delta_C$ 159.7 and 159.8 suggested the spin system consisting of an ortho-substituted phenol group. In addition, correlations observed through long range $^1$H-$^{13}$C between $\delta_H$ 4.69 (H-20a) and $\delta_C$ 168.6 (C-21) as well as $^1$H-$^1$H between $\delta_H$ 5.11 (H-19) and 4.61 (H-20b) interactions indicated the moiety to be a N-terminal 2-hydroxybenzoyl-oxazoline group. Further analysis of the gCOSY and TOCSY spectra indicated at least four more spin systems consisting of a serine (Ser), two modified ornithines (Orns) and a modified alanine (Ala). The modified Orn was defined as $N^\delta$-hydroxy-$N^\delta$-formylornithine (N-OH-N-fOrn) based on the COSY relay observed between $\delta_H$ 4.29 (H-10), 1.82(H-11), 1.68(H-12), 3.45(H-13) and a gHMBC correlation between H-13 and C-14 ($\delta_C$ 164.1). Similarly, another Orn-like spin system potentially related to a piperazic acid (Pip) based on long range $^1$H-$^{13}$C between $\delta_H$ 3.57, 3.63 (H-8)-$\delta_C$ 173.9 (C-9), and a short-range $^1$H-$^1$H array observed from H-5 to H-8. The C-terminal of the peptide was identified as β-alanine (β-Ala) based on COSY correlation between H-3 ($\delta_H$ 3.47, 3.39) to H-2 ($\delta_H$ 2.39) and an HMBC correlation from H-3 to C-1 ($\delta_C$ 174.1). All deduced moieties completed the planar structure of 1.

Cahuitamycin B (2) was isolated by RP-18 HPLC from the same C18 fraction containing compound 1. The HRESIMS [M+H]$^+$ ion peak at m/z 654.2759 provided a molecular formula of $C_{27}H_{39}N_7O_{12}$ with only 12 degree of unsaturation compared to 13 in 1. Moreover, the 1D NMR data although acquired in DMSO-d$_6$, showed high structural similarity to 1 with the existence of six carbonyls (between $\delta_C$ 164.8-171.1), an aldehyde ($\delta_C$ 161.6, $\delta_H$ 8.21) and a phenyl group functionality (between $\delta_C$ 116.7-156.9 and $\delta_H$ 6.81-7.91) fulfilling 11 out of 12 degree of unsaturation. Analysis of the 2D NMR data for 2 suggested a similar carbon backbone as 1 except the gCOSY and HMBC cross peaks at $\delta_C$ 55.4, $\delta_H$ 4.56 (C-16)-$\delta_C$ 61.5, $\delta_H$ 3.58, 3.63 (C-17) and $\delta_C$ 55.2, $\delta_H$ 4.52 (C-19)-$\delta_C$ 61.7, $\delta_H$ 3.69, 3.73 (C-20) indicating two Ser groups, replacing the ring in 1, respectively. Furthermore, similar COSY and HMBC correlation as observed in 1 suggested the presence of Pip, thus accounting for the 12$^{th}$ degree of unsaturation to complete the structure of 2.

Cahuitamycin C (3) was also isolated as a white amorphous solid from the same C18 fraction containing 1 and 2. The HRESIMS [M+H]$^+$ ion peak at m/z 650.2804 provided a molecular formula of $C_{28}H_{39}N_7O_{11}$ with 13 degree of unsaturation. Extensive 1D and 2D NMR analysis indicated that 3 shares structural similarity on much of the carbon backbone compared to 2. The only observed difference was localized to the phenyl ring system where an HMBC correlation from $\delta_H$ 2.51 (H-24) singlet to $\delta_C$ 123.1 (C-25) and 112.8 (C-22) suggested methylation of the N-terminal 2-hydroxybenzoyl-oxazoline group at C-23 ($\delta_C$ 141.2). Furthermore, a change in $^1$H multiplicity at $\delta_H$ 6.73 (H-25) to a doublet confirmed the planar structure of 3.

Stereochemical Studies for Cahuitamycins A-C(1-3)

Due to the polypeptidic nature of the cahuitamycins, advanced Marfey's analysis[13,14] was used to ascertain absolute stereochemistry. Furthermore, initially only cahuitamycin B (2) was selected for acid hydrolysis followed by 1-fluoro-2,4-dintrobenzene-5-alanine amide (FDAA) derivatization. This was based on 2 appearing to be the congener leading to production of cahuitamycins A and C (1 and 3) following cyclization or vice versa.

A study was conducted to compare m/z 357.27, 382.32, and 400.34 channels from LC-ESI-MS chromatograms between the L-FDAA and D, L-FDAA-derivatized Ser, Pip, N-OH-Orn (a hydrolyzed product of N-OH-N-fOrn) products of 1, respectively. Analysis clearly revealed the absolute configuration of the moieties in the hydrolysate of 1 to be L-Ser, L-Ser, D-Pip, D-N-OH-Orn, respectively.

Furthermore, analysis of the Ser, Pip, N—OH—Orn portion of 2 and 3 were conducted as described above for 1, revealing similar stereochemistry. The absolute configuration of the oxazoline ring in 1 and 3 were extrapolated to be D based on similar NMR chemical shifts compared to 2, as well as the absence of any epimerization domain in the biosynthetic gene cluster (FIG. 2).

Affinity of Cahuitamycins Towards Iron

Cahuitamycins were observed to have siderophore like properties, and competition titrations with EDTA were conducted to identify their relative iron-binding affinities.[15] In this method, the Fe-cahuitamycin complex were incubated with varying concentrations of EDTA and detected for Fe distribution using UV-vis spectroscopy. The pFe$^{III}$ for cahuitamycins were calculated against the known stability constants for EDTA (pFe$^{III}$=23.42).[16] Three individual titrations were conducted for each natural product, and the representative pFe$^{III}$ values for cahuitamyicns 1-3 were measured to be 18.34±0.16, 20.42±0.09 and 17.52±0.12, respectively.

Figure 3:
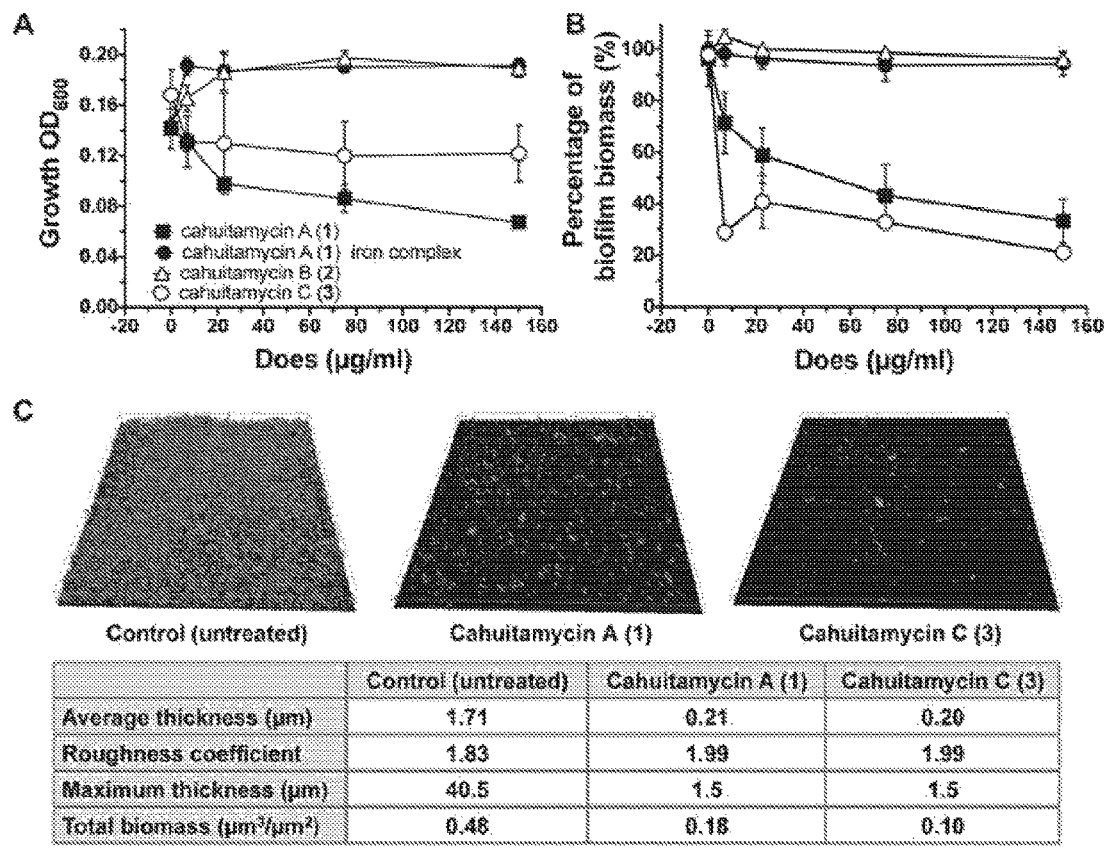
FIG. 3 shows the biological activity of cahuitamycins A-C(1-3) by inhibition of *A. baumannii* growth and biofilm formation by cahuitamycins A-C(1-3) and iron complex of 1.

Interestingly, the observed iron affinities were inversely proportional to the *A. baumannii* biofilm inhibition ability (FIG. 3). This supports a hypothesis that the molecules display diminishing activity over an extended bioassay time course due to iron chelation.

Cahuitamycin Pathway—Polynucleotides, Polypeptides and Mutants Thereof

The term "polynucleotide" refers to a polymer composed of nucleotide units. Polynucleotides include naturally occurring nucleic acids, such as deoxyribonucleic acid (DNA) and ribonucleic acid (RNA) as well as nucleic acid analogs. The term "nucleic acid" typically refers to larger polynucleotides. The term "oligonucleotide" typically refers to shorter polynucleotides, e.g., no greater than about 50 nucleotides. It will be understood that when a nucleotide sequence is represented by a DNA sequence (i.e., A, T, G, C), the nucleotide sequence also encompasses an RNA sequence (i.e., A, U, G, C) in which "U" replaces "T". The term "cDNA" refers to a DNA that is complementary or identical to an mRNA, in either single-stranded or double-stranded form.

The term "expression control sequence" refers to a nucleotide sequence that regulates the expression of a nucleotide sequence operatively linked thereto. The term "operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible, repressible, or constitutive), enhancers, transcription terminators, a start codon (e.g., ATG), splicing signals for introns, and stop codons.

The term "recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is also known as a "recombinant host cell". The gene is then expressed in the recombinant host cell to produce, e.g., a "recombinant polypeptide". A recombinant polynucleotide may serve a non-coding function (e.g., promoter, origin of replication, ribosome binding site, transcription factor binding site, and the like) as well.

The terms "polypeptide" and "protein" refer to a polymer composed of amino acid residues, related naturally occurring structural variants, and/or synthetic non-naturally occurring analogs thereof, linked via peptide bonds or peptide bond isosteres. Synthetic polypeptides can be synthesized, e.g., using an automated polypeptide synthesizer. The terms "polypeptide" and "protein" are not limited to a minimum length of the product. The term "protein" typically refers to larger polypeptides. The term "peptide" typically refers to shorter polypeptides. Thus, peptides, oligopeptides, dimers, multimers, and the like, are included within the definition. Both full-length proteins and fragments thereof are encompassed by the definition. The terms "polypeptide" and "protein" may also include post-expression modifications of the polypeptide or protein, e.g., glycosylation, acetylation, phosphorylation, and the like. Unless stated to the contrary, a post-expression modification characteristic of a wild-type polypeptide or protein is embraced by the simple recitation of the term "polypeptide" or "protein." A post-expression modification not characteristic of a wild-type polypeptide or protein is referred to as a modified polypeptide or a modified protein. Such modified forms may arise from post-expression modifications of a wild-type amino acid sequence wherein the modification(s) is/are not characteristic of the wild-type form, or post-expression modification of a non-wild-type polypeptide or protein. Furthermore, for purposes of the present disclosure, a "polypeptide" can include "modifications," such as deletions, additions, substitutions (which may be conservative in nature or may include substitutions with any of the 20 amino acids that are commonly present in human proteins, or any other naturally or non-naturally-occurring or atypical amino acids), and chemical modifications (e.g., addition of or substitution with peptidomimetics), to the native sequence of amino acids. These modifications may be deliberate, as through site-directed mutagenesis, or through chemical modification of amino acids to remove or attach chemical moieties, or may be accidental, such as through mutations arising with hosts that produce the proteins or through errors due to PCR amplification.

Conventional notation is used herein to portray polypeptide sequences: the left-hand end of a polypeptide sequence is the amino-terminus; the right-hand end of a polypeptide sequence is the carboxyl-terminus.

The term "conservative substitution" refers to substitution of an amino acid in a polypeptide with a functionally, structurally or chemically similar natural or unnatural amino acid. In certain embodiments, the following groups each contain natural amino acids that are conservative substitutions for one another:

(1) Glycine (G), Alanine (A);
(2) Aspartic acid (D), Glutamic acid (E);
(3) Asparagine (N), Glutamine (Q);
(4) Arginine (R), Lysine (K);
(5) Isoleucine (I), Leucine (L), Methionine (M), Valine (V), Alanine (A);
(6) Phenylalanine (F), Tyrosine (Y), Tryptophan (W); and
(7) Serine (S), Threonine (T), Cysteine (C).

In other embodiments, amino acids may be grouped as set out below:

(1) hydrophobic: Met, Ala, Val, Leu, Be, Phe, Trp;
(2) neutral hydrophilic: Cys, Ser, Thr, Asn, Gln;
(3) acidic: Asp, Glu;
(4) basic: His, Lys, Arg;
(5) residues that influence backbone orientation: Gly, Pro; and
(6) aromatic: Trp, Tyr, Phe, His.

In certain embodiments, the peptides or polypeptides described herein are generated via recombinant means, using a polynucleotide encoding a Cah-derived peptide or variant thereof. The disclosure thus encompasses polynucleotides encoding any of the Cah-derived peptides and variants thereof described herein, host cells and vectors comprising such polynucleotides, optionally linked to expression control sequences, host cells comprising such vectors, and methods of using such polynucleotides, vectors and host cells to produce Cah-derived peptides and variants thereof. Cah-derived peptides and variants thereof expressed by such polynucleotides can be produced by methods including growing host cells in culture medium under conditions suitable for expression of the polynucleotide encoding an Cah-derived peptide or variant thereof, and isolating the expression product from the host cells or culture medium. Actual expression products may vary from the encoded protein product depending on any post-translational processing.

The term "chimera" as used herein refers to a polynucleotide or polypeptide comprising at least two heterologous polynucleotide or polypeptide sequences (i.e., derived from different sources or not associated with each other as a naturally occurring sequence) which are directly or indirectly attached or linked together using techniques commonly known in the art, e.g., recombinant expression or chemical crosslinking. In certain embodiments, a heterologous sequence comprises a protein or peptide directly or indirectly linked to a Cah-derived peptide or variant thereof, including proteins or peptides that are cleavable from the Cah peptide or variant. In further embodiments, Cah variants are chimeras, as described herein.

In certain embodiments, fusions such as chimeras include Cah fusion proteins comprising a cleavable carrier protein or peptide tag. The term "cleavable carrier protein" or "cleavable peptide tag" refers to a peptide or polypeptide sequence that may be fused, directly or indirectly via a linker, to a heterologous polypeptide sequence (e.g., a Cah-related polypeptide), and is removable from the heterologous sequence using an agent that cleaves or separates the cleavable peptide or polypeptide from the heterologous polypeptide or protein. In certain embodiments, the cleavable carrier protein or peptide tag improves generation, purification and/or detection of the fusion protein or the heterologous polypeptide. Exemplary cleavable carrier proteins and peptide tags include, but are not limited to, human transcription factor TAF12 (TAF12), ketosteroid isomerase (KSI), maltose-binding protein (MBP), β-galactosidase (13-Gal), glutathione-S-transferase (GST), thioredoxin (Trx), chitin-binding domain (CBD), BMP-2 mutation (BMPM), SUMO, CAT, TrpE, staphylococcal protein A, streptococcal proteins, starch-binding protein, cellulose-binding domain of endoglucanase A, cellulose-binding domain of exoglucanase Cex, biotin-binding domain, recA, Flag, c-Myc, poly(His), poly(Arg), poly(Asp), poly(Gln), poly(Phe), poly(Cys), green fluorescent protein, red fluorescent protein, yellow fluorescent protein, cayenne fluorescent protein, biotin, avidin, streptavidin, an antibody epitope, and a fragment thereof.

A "cleaving agent" is an agent that is useful for cleaving or separating, e.g., a cleavable peptide or polypeptide from a heterologous polypeptide or protein such as a Cah-related polypeptide or protein. Exemplary chemical and proteolytic cleaving agents (cleavage sites in parenthesis) include, without limitation, palladium, cyanogen bromide (CNBr; M-X), formic acid (D-P), hydroxylamine (N-G), clostripain, thrombin, chymotrypsin, trypsin, trypsin-like proteases, carboxypeptidase, enterokinase (enteropeptidase; DDDDK-X), Kex 2 protease, Omp T protease, Factor Xa protease (IEGR-X), subtilisin, proTEV (EXXYXQ-G), SUMO protease, V8 protease, HIV protease, rhinovirus protease, furilisin protease, IgA proteases, human Pace protease, collagenase, Nia protease, poliovirus 2Apro protease, poliovirus 3C protease, genenase, furin, elastase, Proteinase K, pepsin, rennin (chymosin), microbial aspartic proteases, papain, calpain, chymopapain, ficin (ficain), bromelain (bromelase), cathepsin B, caspases, thermolysin, Endoprotease Arg-C, Endoprotease Glu-C, Endoprotease Lys-C, kallikrein, plasmin, and protein self-cleavage, where "X" denotes any amino acid.

The terms "identical" and percent "identity", in the context of two or more polynucleotide or polypeptide sequences, refer to two or more sequences or subsequences that are the same or have a specified percentage of nucleotides or amino acid residues that are the same, when compared and aligned for maximum correspondence, as measured using one of the following sequence comparison algorithms or by visual inspection.

In certain embodiments, the term "substantially homologous" or "substantially identical", in the context of two nucleic acids or polypeptides, refers to two or more sequences or subsequences that have at least about 40%, 45%, 50%, 55%, 60%, 65%, 70%, 75%, 80%, 85%, 90%, 91%, 92%, 93%, 94%, 95%, 96%, 97%, 98% or 99% identity of nucleotides or amino acid residues, when compared and aligned for maximum correspondence, as measured using one of the following sequence comparison algorithms or by visual inspection. In certain embodiments, the substantial homology or identity exists over regions of the sequences that are at least about 20, 30, 40, 50, 60, 70, 80, 90, 100 or 150 residues in length. In other embodiments, the sequences are substantially homologous or identical over the entire length of either or both comparison nucleic acids or polypeptides.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math., 2:482 (1981), by the homology alignment algorithm of Needleman & Wunsch, J. Mol. Biol., 48:443 (1970), by the search for similarity method of Pearson & Lipman, Proc. Natl. Acad. Sci. USA, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection. One example of a useful algorithm is PILEUP, which uses a simplification of the progressive alignment method of Feng & Doolittle, J. Mol. Evol., 35:351-360 (1987) and is similar to the method described by Higgins & Sharp, CABIOS, 5:151-153 (1989). Another algorithm useful for generating multiple alignments of sequences is Clustal W (Thompson et al., Nucleic Acids Research, 22:4673-4680 (1994)). An example of an algorithm that is suitable for determining percent sequence identity and sequence similarity is the BLAST algorithm (Altschul et al., J. Mol. Biol., 215:403-410 (1990); Henikoff & Henikoff, Proc. Natl. Acad. Sci. USA, 89:10915 (1989); Karlin & Altschul, Proc. Natl. Acad. Sci. USA, 90:5873-5787 (1993)). Software for performing BLAST analyses is publicly available through the National Center for Biotechnology Information.

In certain embodiments, two nucleic acid or polypeptide sequences are substantially homologous or identical if the polypeptide encoded by the first nucleic acid is immunologically cross-reactive with the polypeptide encoded by the second nucleic acid. In further embodiments, a polypeptide is substantially homologous or identical to a second polypeptide where the two polypeptides differ only by conservative substitutions. In other embodiments, two nucleic acid sequences are substantially homologous or identical if the two molecules hybridize to each other under stringent conditions, as described herein.

The term "wild-type" ("wt") refers to the natural form, including sequence, of a polynucleotide, polypeptide or protein in a species. Where more than one form is found in nature and the knowledge in the art has not identified a single form as the wild-type, the "wild-type" is the natural form found in greatest frequency. A wild-type form is distinguished from a mutant form of a polynucleotide, polypeptide or protein arising from genetic mutation(s).

In certain embodiments, a polypeptide that is an "analog" or "variant" of a wild-type polypeptide is a polypeptide having at least about 30%, 40%, 50%, 60%, 70%, 80%, 90%, 95%, 96%, 97%, 98% or 99% sequence homology with the wild-type polypeptide. Such analogs or variants can be comprised of non-naturally occurring amino acid residues, including without limitation homoarginine, ornithine, penicillamine and norvaline, as well as naturally occurring amino acid residues. Such analogs or variants can also be composed of one or more D-amino acid residues, and can also contain peptidomimetics or peptide bond isosteres, such as non-peptide linkages between two or more amino acid or peptidomimetic residues.

In certain embodiments, the analog or variant polypeptide has one or more deletions, additions, and/or substitutions with natural amino acids, unnatural amino acids and/or peptidomimetics with respect to the amino acid sequence of the wild-type polypeptide. In further embodiments, the analog or variant polypeptide has a moiety (e.g., a polymer, such as PEG, or a heterologous peptide sequence) directly or indirectly attached to it which is not present in the wild-type polypeptide, even if the polypeptides share 100% homology in their corresponding amino acid sequences.

In certain embodiments, in addition to or alternatively to amino acid addition(s), deletion(s) and/or substitution(s), the Cah variants are conjugated at the N-terminus, the C-terminus and/or internal site(s) to any of the moieties described herein, including but not limited to moieties that reduce renal clearance (e.g., negatively charged PEG moieties), hydrophilic polymers (e.g., PEG), peptide sequences of one or more amino acids and derived from natriuretic polypeptides (e.g., NPPA, ANP, NPPB, BNP) or non-natriuretic polypeptides (e.g., serum albumins, immunoglobulins), carbohydrates (e.g., carbohydrates recognized by receptors on the surface of diseased (e.g., tumor and cancer) cells), hydrophobic acids (e.g., $C_5$-$C_{12}$ carboxylic acids, natural fatty acids), and combinations thereof.

Other Cah variants, including truncated Cah peptides having wild-type sequences or amino acid addition(s), deletion(s) and/or substitution(s), can also be found in a fusion protein.

The Cah peptides and variants described herein can be conjugated to one or more hydrophilic polymers, which may be the same or different, at the N-terminus, the C-terminus, and/or one or more internal sites. For purposes of explanation and brevity, polyethylene glycol (i.e., PEG or polyethylene oxide (PEO)) will be used as a representative example of a hydrophilic polymer. Various sites of PEGylation of a Cah polypeptide are possible, including but not limited to: (1) PEGylation only at the N-terminus; (2) PEGylation only at the C-terminus; (3) PEGylation only at one or more internal sites; (4) PEGylation at both the N-terminus and the C-terminus; (5) PEGylation at the N-terminus and one or more internal sites; (6) PEGylation at the C-terminus and one or more internal sites; and (7) PEGylation at the N-terminus, the C-terminus and one or more internal sites. In some embodiments, Cah polypeptides are PEGylated only at the N-terminus. In other embodiments, Cah polypeptides are PEGylated only at one or more internal sites. In yet other embodiments, Cah polypeptides are PEGylated at the N-terminus and one or more internal sites.

Non-limiting examples of hydrophilic polymers include polymers formed from carboxylic acid-bearing monomers (e.g., methacrylic acid (MA) and acrylic acid (AA)), polyvinyl alcohols, polymers formed from hydroxyl-bearing monomers (e.g., hydroxyethyl methacrylate (HEMA), hydroxypropyl methacrylate (HPMA), hydroxypropyl methacrylamide, and 3-trimethylsilylpropyl methacrylate (TM-SPMA)), polyalkylene oxides, polyoxyethylated polyols (e.g., glycerol), polyethylene glycol (PEG), polypropylene glycol, mono-$C_1$-$C_{10}$ alkoxy-PEGs (e.g., monomethoxy-PEG), tresyl monomethoxy-PEG, aryloxy-PEGs, PEG acrylate (PEGA), PEG methacrylate, PEG propionaldehyde, bis-succinimidyl carbonate PEG, copolymers of 2-methacryloyloxyethyl-phosphorylcholine (MPC) and N-vinyl pyrrolidone (VP), hydroxy functional poly(N-vinyl pyrrolidone) (PVP), SIS-PEG (SIS is polystyrene-polyisobutylene-polystyrene block copolymer), polystyrene-PEG, polyisobutylene-PEG, PCL-PEG (PCL is polycaprolactone), PLA-PEG (PLA is polylactic acid), PMMA-PEG (PMMA is poly(methyl methacrylate)), PDMS-PEG (PDMS is polydimethyloxanone), PVDF-PEG (PVDF is polyvinylidene fluoride), PLURONIC™ surfactants (polypropylene oxide-co-polyethylene glycol), poly(tetramethylene glycol), poly (L-lysine-g-ethylene glycol) (PLL-g-PEG), poly(L-lysine-g-hyaluronic acid) (PLL-g-HA), poly(L-lysine-g-phosphoryl choline) (PLL-g-PC), poly(L-lysine-g-vinyl pyrrolidone) (PLL-g-PVP), poly(ethyleneimine-g-ethylene glycol) (PEI-g-PEG), poly(ethyleneimine-g-hyaluronic acid) (PEI-g-HA), poly(ethyleneimine-g-phosphoryl choline) (PEI-g-PC), poly(ethyleneimine-g-vinyl pyrrolidone) (PEI-g-PVP), PLL-co-HA, PLL-co-PC, PLL-co-PVP, PEI-co-PEG, PEI-co-HA, PEI-co-PC, PEI-co-PVP, cellulose and derivatives thereof (e.g., hydroxyethyl cellulose), dextran, dextrins, hyaluronic acid and derivatives thereof (e.g., sodium hyaluronate), elastin, chitosan, acrylic sulfate, acrylic sulfonate, acrylic sulfamate, methacrylic sulfate, methacrylic sulfonate, methacrylic sulfamate, polymers and copolymers thereof, and polymers and copolymers of combinations thereof.

The Cah peptides and variants disclosed herein can be prepared by standard solid-phase peptide synthesis methods, with natural or unnatural amino acid(s) or peptidomimetic(s) optionally being substituted and/or added where appropriate. The Cah peptides and variants can also be produced by recombinant synthesis processes, e.g., via fusion proteins containing a tag or carrier protein, wherein use of the tag or carrier protein facilitates, e.g., detection, isolation and/or purification of the fusion protein, and selective chemical or proteolytic cleavage of the tag or carrier protein from the fusion protein provides the target Cah peptide or variant. PEGylation of Cah peptides and variants can be conducted following, or as part of, chemical or biological synthesis of the Cah compounds, with the conjugation reaction being performed by N-Hydroxysuccinimide—(NHS-) or aldehyde-based chemistry or other chemistry known in the art.

The Cah peptides and variants can be synthesized using a peptide synthesizer and purified according to methods known in the art, e.g., according to the methods of Atherton and Sheppard, Solid Phase Peptide Synthesis: a Practical Approach, IRL Press (Oxford, England (1989)).

The Cah-derived peptides and variants thereof can be recombinantly produced, e.g., via a fusion protein process, wherein the fusion protein comprises a Cah peptide or variant, and a cleavable peptide or protein, or peptide tag. In certain embodiments, the recombinant process comprises culturing in a medium a host cell comprising a polynucleotide encoding a Cah peptide or variant linked to a polynucleotide encoding a cleavable peptide or protein, under conditions that result in expression of a fusion polypeptide encoded by the polynucleotides. In certain embodiments, the host cell is transformed with an expression vector comprising a polynucleotide encoding a Cah peptide or variant linked to a polynucleotide encoding a cleavable peptide or protein. In certain embodiments, the fusion polypeptide is expressed as a soluble protein or as an inclusion body. The expressed fusion polypeptide can be isolated from the host cell or culture medium, and the isolated fusion polypeptide can be contacted with a cleaving agent to release the Cah peptide or variant.

Recombinant Cah polynucleotides and polypeptides can be expressed in an expression vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, including without limitation cosmids, plasmids (e.g., naked or contained in liposomes) and viruses that incorporate the recombinant polynucleotide. The expression vector is inserted into an appropriate host cell for expression of the polynucleotide and polypeptide via transformation or transfection using techniques known in the art. See, e.g., Sambrook, Fritsch & Maniatis, Molecular Cloning: A Laboratory Manual, 2nd Ed., Cold Spring Harbor Laboratory Press (Cold Spring Harbor, N.Y. (1989)).

In some embodiments, the expression vector is a plasmid. In certain embodiments, the plasmid is selected from the group consisting of pET-21a, pJexpress, pET-31b, pET-15b, pET-32a, pET-41a, pMAL, pQE-30, pET-SUMO, pET-22b, pKC1139, pYJ276, and pTYB11.

An expression construct can express a fusion protein comprising a Cah peptide or variant, and a carrier protein or tag. The tag can be an amino acid sequence that confers a useful property to the fusion protein, e.g., that facilitates detection, isolation and/or purification of the fusion protein. In certain embodiments, the tag is a ligand-binding domain that can be used to purify the fusion protein by applying the fusion protein to separation media containing the ligand. For example, a fusion protein comprising a glutathione-S-transferase (GST) domain can be applied to a chromatographic column containing glutathione-linked separation media. As another example, a fusion protein comprising maltose-binding protein (MBP) as a tag can be applied to separation media containing maltose. As a further example, a fusion protein comprising a polyhistidine tag can be applied to a nickel column, whereby chelation of the polyhistidine tag to the nickel column facilitates purification of the fusion protein. In other embodiments, the tag is a ligand. For example, a fusion protein can comprise glutathione as a tag and can be applied to a chromatographic column containing glutathione-S-transferase-linked separation media.

Non-limiting examples of carrier proteins and tags for use in fusion proteins include histidine (e.g., hexa-His) tags, poly(His), poly(Arg), poly(Asp), poly(Gln), poly(Phe), poly(Cys), and the above-noted cleavable carrier proteins or peptide tags, including human transcription factor TAF12 (TAF12), ketosteroid isomerase (KSI), maltose-binding protein (MBP), β-galactosidase (β-Gal), glutathione-S-transferase (GST), thioredoxin (Trx), chitin-binding domain (CBD), BMP-2 mutation (BMPM), SUMO, CAT, TrpE, staphylococcal protein A, streptococcal proteins, starch-binding protein, cellulose-binding domain of endoglucanase A, cellulose-binding domain of exoglucanase Cex, biotin-binding domain, recA, Flag, c-Myc, poly(His), poly(Arg), poly(Asp), poly(Gln), poly(Phe), poly(Cys), green fluorescent protein, red fluorescent protein, yellow fluorescent protein, cayenne fluorescent protein, biotin, avidin, streptavidin, an antibody epitope, and a fragment thereof.

To generate the target Cah peptide or variant, the carrier protein or tag can be cleaved from the fusion protein by means of chemical cleavage, protease cleavage, or protein self-cleavage. Exemplary chemical and proteolytic cleavage agents are provided above.

Due to the nature of the particular kinds of chemical cleavage, cleavage using formic acid may generate Pro-Cah, CNBr may generate Cah having Met-to-Asn substitution, and hydroxylamine may generate Gly-Cah. Alternatively, chemical or protease cleavage may be avoided by using particular constructs (e.g., pET-21a-Cah) that express Cah peptides or variants not as fusion proteins. Expression of pET-21a-Cah may produce Met-Cah. In addition, certain fusion proteins (e.g., those containing intein-Cah) can undergo self-cleavage to generate Cah. In some embodiments, a Cah polypeptide may be fused to an intein that is, in turn, fused to a cleavable agent, carrier polypeptide or tag.

In additional embodiments, a fusion protein comprises a cleavable peptide linker between a Cah peptide or variant, and a carrier protein or tag. In certain embodiments, the cleavable peptide linker is selected from the group consisting of Asp-Pro, Asn-Gly, Met-X, Val-Asp-Asp-Arg, Gly-Ser-Asp-Arg, Ile-Thr-Asp-Arg, Pro-Gly-Asp-Arg, Ile-Glu-Gly-Arg-X, Asp-Asp-Asp-Asp-Lys-X, Glu-X-X-Tyr-X-Gln-Gly, and Ala-Phe-Leu-Gly-Pro-Gly-Asp-Arg, where X denotes an amino acid. In further embodiments, the cleavable peptide linker is cleaved by a cleaving agent selected from the group consisting of palladium, cyanogen bromide (CNBr), formic acid, hydroxylamine, clostripain, thrombin, chymotrypsin, trypsin, trypsin-like proteases, carboxypeptidase, enterokinase (enteropeptidase), Kex 2 protease, Omp T protease, Factor Xa protease, subtilisin, proTEV, SUMO protease, V8 protease, HIV protease, rhinovirus protease, furilisin protease, IgA proteases, human Pace protease, collagenase, Nia protease, poliovirus 2Apro protease, poliovirus 3C protease, genenase, furin, elastase, Proteinase K, pepsin, rennin (chymosin), microbial aspartic proteases, papain, calpain, chymopapain, ficin (ficain), bromelain (bromelase), cathepsin B, caspases, thermolysin, Endoprotease Arg-C, Endoprotease Glu-C, Endoprotease Lys-C, kallikrein, and plasmin.

Host cells used to produce Cah peptides and variants as described herein can be bacterial, yeast, insect, non-mammalian vertebrate, or mammalian cells. In some embodiments, the host cells are bacterial, e.g., *E. coli*. In certain embodiments, the *E. coli* cells are selected from the group consisting of BL21, BL21(DE3), BL21(DE3)pLysS, BL21(DE3)pGro7, ArcticExpress(DE3), C41, C43, Origami B(DE3), Origami B(DE3)pLysS, KRX, and Tuner(DE3). Non-limiting examples of mammalian cells include hamster, monkey, chimpanzee, dog, cat, bovine, porcine, mouse, rat, rabbit, sheep and human cells. The host cells can be immortalized cells (a cell line) or non-immortalized (primary or secondary) cells and can be any of a wide variety of cell types, such as, but not limited to, fibroblasts, keratinocytes, epithelial cells (e.g., mammary epithelial cells, intestinal epithelial cells), ovary cells (e.g., Chinese hamster ovary (CHO) cells), endothelial cells, glial cells, neural cells, formed elements of the blood (e.g., lymphocytes, bone marrow cells), chondrocytes and other bone-derived cells, and precursors of these somatic cell types. Host cells containing the DNA or RNA encoding the Cah peptide or variant are cultured under conditions appropriate for growth of the cells, expression of the DNA or RNA, and identification/selection of cells expressing the Cah peptide or variant.

Dissecting the Cahuitamycin Biosynthetic Gene Cluster

Figure 2B:
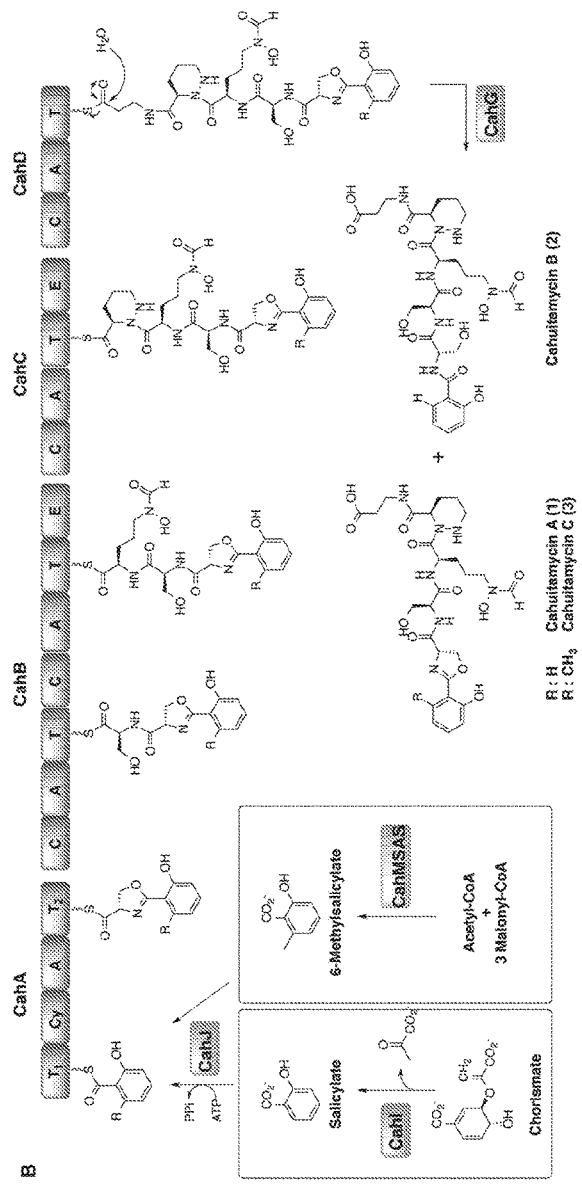

In order to mine a candidate gene cluster for cahuitamycin biosynthesis, analysis of the draft genome sequence of *S. gandocaensis* was performed using antiSMASH.[17] As a result, one candidate gene cluster responsible for nonribosomal peptide scaffold biosynthesis, transport, and regulation of cahuitamycins A and B (1 and 2) were identified (FIG. 2A). Cahuitamycin C (3) biosynthesis was initially expected to involve SAM-dependent C-methyltransferase through post-tailoring modification. However, the absence of genes responsible for the formation of a methyl group at C23 position of 3 near cluster 1 led to the hypothesis that perhaps another standalone gene cluster 6-methyl salicyclate synthase (6-MSAS) might be involved in the biosynthesis of 3 (FIG. 2). The architecture and annotation of the bifurcated cahuitamycin (cah) gene cluster is shown in FIG. 2 and Table 1, respectively. The cluster containing NRPS encoding genes cahA-B-C-D, together with genes involved in chain initiation (cahI-J), termination (cahG), and transcriptional regulation (cahR) is located in a region spanning about 40 kb of DNA. Each NRPS protein consists of the essential condensation (C), adenylation (A), and thiolation protein (T) domains (FIG. 2B), and has a non-co-linear architecture.

CahA is proposed to catalyze oxazoline ring formation together with a putative salicylate synthase CahI and salicylate-AMP ligase CahJ (FIG. 2B). CahI is homologous to MbtI of *Mycobacterium tuberculosis* and is predicted to convert chorismate to salicylate (FIG. 2B).[19] CahJ bears high similarity to a salicylate-AMP ligase MxcE from *Sorangium cellulosum* So ce56,[20] which suggests that it activates the salicylate by adenylation (FIG. 2B). The identity of amino acid building blocks activated by the Cah NRPS were analyzed by examining the specificity-conferring residues in each A domain (Table 2)[21]. The A domain in CahA is predicted to recognize L-Cys (Table 2), though only L-Ser is loaded according to the structure of cahuitamycins, which is also observed in the amychelin biosynthetic system.[18] The heterocyclization between Ser and the carbonyl group to form an oxazoline ring scaffold can be attributed to the Cy domain in CahA, and the resulting peptide product is then transferred to CahB for synthesis of 1 and 3. Similar to gobichelins formation, where oxazoline ring of gobichelin A is hydrolyzed into a linear form under non-acidic condition, 1 may convert to 2 with a free Ser through hydrolysis of the oxazoline ring.[22] The in silico analysis of A domains in CahB predicts activation of L-Ser and L-N-OH-N-fOrn by CahB-$A_1$ and CahB-$A_2$, respectively (Table 2). Subsequent to the incorporation of L-Ser by CahB-$A_1$, a L-N-OH-N-fOrn moiety, which is synthesized from L-Orn by a putative Orn hydroxylase (CahMO) and a putative formyltransferase

TABLE 1

| Protein. | Amino acid | Proposed function | Sequence similarity, Organism | Identity/ Similarity (%) | GenBank accession no. |
|---|---|---|---|---|---|
| CahFT | 317 | Formyltransferase | SCAB_85511, *Streptomyces scabies* | 81/90 | ELP64051 |
| CahMO | 451 | L-ornithine-5-monooxygenase | STRTUCAR8_09254, *Streptomyces turgidiscabies* Car8 | 72/81 | CBG75496 |
| CahT1 | 338 | Putative iron(III)/siderophore ABC transporter substrate binding protein | FhuD, *Actinoplanes missouriensis* 431 | 36/57 | BAL90510 |
| CahA | 1159 | NRPS (T Cy A T) | NRPS, *Streptomyces viridochromogenes* | 82/87 | ELS51167 |
| CahB | 2626 | NRPS (C A T C A T E) | NRPS, *Streptomyces viridochromogenes* | 80/85 | ELS51166 |
| CahC | 1503 | NRPS (C A T E) | NRPS, *Rhodococcus opacus* | 45/57 | BAH53136 |
| CahD | 1057 | NRPS (C A T) | NRPS, *Streptomyces* sp. NRRL F-4415 | 51/62 | AGE11899 |
| CahE | 72 | MbtH-like protein | MbtH, *Streptomyces viridochromogenes* | 82/92 | ELS51232 |
| CahF | 162 | Aspartate 1-decarboxylase | PanD, *Amycolatopsis mediterranei* U32 | 78/84 | ADJ46798 |
| CahG | 270 | α/β hydrolase | LipE, *Streptomyces albus* J1074 | 64/76 | EFE82037 |
| CahH | 424 | Siderophore export protein | SACE_2690, *Saccharopolyspora erythraea* NRRL 2338 | 64/75 | CAM01972 |
| CahI | 425 | Salicylate synthase | MbtI, *Mycobacterium tuberculosis* UT205 | 43/57 | CCE37856 |
| CahJ | 544 | Salicylate-AMP ligase | MxcE, *Sorangium cellulosum* So ce56 | 64/74 | CAN94040 |
| CahT2 | 323 | Iron ABC transporter permease | STVIR_7837, *Streptomyces viridochromogenes* | 89/92 | ELS51226 |
| CahT3 | 353 | Iron ABC transporter permease | STVIR_7836, *Streptomyces viridochromogenes* | 88/94 | ELS51225 |
| ORF1 | 595 | FAD/iron sulfur cluster binding oxidoreductase | B479_00040, *Pseudomonas putida* HB3267 | 36/49 | AGA70926 |
| ORF2 | 361 | Peptidase C45, acyl-coenzyme A/6-aminopenicillanic acid acyl-transferase | SACE_5325, *Saccharopolyspora erythraea* NRRL 2338 | 51/62 | CAM04564 |
| ORF3 | 344 | 6-aminohexanoate-oligomer hydrolase | Ny1C, *Flavobacterium* sp. | 60/73 | BAA01528 |
| CahT4 | 251 | ABC transporter ATPase | OppF, *Agromyces* sp. KY5R | 60/71 | BAE97623 |
| CahT5 | 329 | ABC transporter ATPase | Vapar_6007, *Variovorax paradoxus* | 51/65 | ACS22576 |
| CahT6 | 286 | ABC transporter permease | OppC, *Agromyces* sp. KY5R | 69/83 | BAE97625 |
| CahT7 | 323 | ABC transporter permease | OppB, *Agromyces* sp. KY5R | 56/76 | BAE97626 |
| CahT8 | 535 | Extracellular solute-binding Protein | OppA, *Agromyces* sp. KY5R | 52/70 | BAE97627 |
| CahR | 333 | LacI-family transcriptional regulator | SSEG_04729, *Streptomyces sviceus* ATCC29083 | 74/83 | EDY58149 |
| CahMSAS | 1760 | 6-methylsalicylic acid synthase | Ch1B1, *Streptomyces antibioticus* | 56/78 | AAZ77673 |

(CahFT), is appended to the growing chain (Table 1). The L-N-OH-N-fOrn moiety linked to the T domain of CahB module 3 undergoes epimerization by the epimerase (E) domain,[23,24] which is consistent with the stereochemistry of cahuitamycins.

TABLE 2

| A domain | active site residues | predicted substrate |
|---|---|---|
| CahA-A | D L Y N L G L I H K (SEQ ID NO: 3) | L-Cys |
| CahB-A$_1$ | D V W H V S L V D K (SEQ ID NO: 4) | L-Ser |
| CahB-A$_2$ | D I N Y W G G I G K (SEQ ID NO: 5) | L-fhOrn |
| CahC-A | D A W E G G L V D K (SEQ ID NO: 6) | L-Gln |
| CahD-A | I D V T I S L A D K (SEQ ID NO: 7) | L-β-Ala |

Biosynthesis of cahuitamycins involves formation and loading of the piperazic acid (Pip) building block into the growing peptide chain. Although, the relatively rare Pip moiety is found in several biologically active secondary metabolites,[25-30] the precise biosynthetic events for Pip elaboration has not been elucidated. Recent feeding experiments have suggested that generation of Pip moiety in kutzneride occurs prior to incorporation into the respective peptide chain,[26] similar to the formation of a hydrazo linkage in valanimycin.[25] It is likely that the biosynthesis of the piperazate moiety in cahuitamycin is initiated by N-hydroxylation of the amino group of Orn by a putative CahMO. The resulting L-N-OH-Orn residue attached to the T domain of CahC is converted to its corresponding D-stereoisomer (D-N-OH-Orn) by the E domain within the same module followed by nucleophilic attack of the amino group to close the ring. Alternatively, since the A domain in the CahC is homologous to L-glutamine (Gln) activating A domains (Table 2), it is possible that Gln may be incorporated as a branch point from primary metabolism into the piperazate biosynthetic pathway (FIG. 2).[31,32]

Further in silico analysis of the A domain in CahD (Table 2) predicted loading of β-Ala onto the T domain consistent with the structure of cahuitamycins. Also, it further affirms that the presence of β-Ala residue is likely formed from L-aspartate (L-Asp) by the cahF gene product.[33] The CahD contains neither C-terminal thioesterase nor a reductase domain usually required for chain release in nonribosomal peptide biosynthesis, and likely involves a specific hydrolase for the release of fully assembled peptide chain from the T domain of the last module CahD. Following final extension by β-Ala, CahG (α/β hydrolase superfamily) catalyzes in trans release of the peptide chain through hydrolysis of the T domain-bound thioester as described previously in coelichelin biosynthesis.[34]

Moreover, CahE, an MbtH-like protein homolog, likely contributes to the stimulation of A domains in Cah NRPS as described previously.[35] CahH, which belongs to the major facilitator superfamily, is similar to EntS, an entrobactin efflux exporter of E. coli. Proteins coded by CahT1 through CahT8 are putatively required for iron uptake and translocation of cahuitamycin produced across the membrane (Table 1). Therefore, these proteins might be involved in export of cahuitamycins from the cytoplasm into the medium. ORF1, ORF2 and ORF3, show sequence similarity to oxidoreductase, acyl-transferase, and 6-aminohexanoate-oligomer hydrolase, respectively, and their relationship to cahuitamycin biosynthesis is unclear (Table 1).

Biosynthesis of Cahuitamycin C

The function of the assigned biosynthetic cluster was confirmed by deletion of cahI in S. gandocaensis through insertion of kanamycin resistance gene (aph). Surprisingly, the ΔcahI S. gandocaensis DHS334 led to the selective production of 3, while the production of 1 and 2 were completely abolished. This result confirmed that the 6-methylsalicylate starter unit is derived directly from the 6-methylsalicylate synthase (6-MSAS), which is then adenylated by CahJ and loaded onto the T$_1$ domain of CahA for production of 3. A BLAST search using bacterial 6-MSASs including various putative candidates from microbes,[18,36-38] led to the identification of an unlinked iterative type I PKS gene encoding a 6-MSAS that is located at about 50 kb away from the cluster 1 based on the draft sequencing data (FIG. 2).[39-40] Like other bacterial 6-MSAS, cahuitamycin 6-MSAS (Cluster 2; CahMSAS) possesses keto synthase (KS), acyltransferase (AT), dehydratase (DH), ketoreductase (KR), and acyl carrier protein (ACP) on a single protein (Table 1). Feeding exogenous 6-methylsalicylic acid into the culture of ΔcahI strain resulted in an increased production of 3, while no changes were observed in production of 1 and 2. Furthermore, production of 1 and 2 was restored by external supplementation of salicylic acid to the ΔcahI growth medium, representing chemical complementation and confirmation of its role in the production of cahuitamycins. These studies substantiate that the biosynthesis of 3 is independent of cahI-mediated salicylic acid biosynthesis and more importantly cahuitamycins are derived from a bifurcated biosynthetic pathway (FIG. 2). The observation provides an intriguing example where S. gandocaensis is diversifying its biosynthetic machinery to produce a more potent/toxic molecule to provide a competitive advantage in its natural habitat.

Mutasynthetic Generation of Cahuitamycin Analogs

The biosynthetic process for generating 3 revealed the possible tolerance of CahJ towards structurally related salicylic acid substrates and a promising avenue for generating new cahuitamycin analogs by mutasynthesis. In this approach, the DHS334 ΔcahI strain was provided with a series of substituted benzoic acid substrates (2-hydroxybenzoic acid, 2,3-dihydroxybenzoic acid, 2,4-dihydroxybenzoic acid, 2-fluorobenzoic acid, 2-hydoxy-5-methylbenzoic acid (5-methylsalicylic acid), 2-hydoxy-6-methylbenzoic acid (6-methylsalicylic acid, 2-cholorbenzoic acid) and sequentially assessed their incorporation to generate new analogs. Of the series of unnatural starter units tested, incorporation of methyl-hydroxy benzoic acid substrates showed some level of incorporation. Incorporation of 5-methylsalicylic acid into the ΔcahI pathway provided a new analog cahuitamycin D (4).

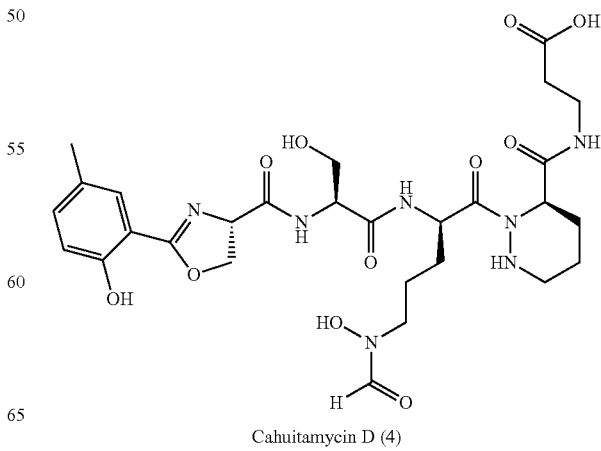

Cahuitamycin D (4)

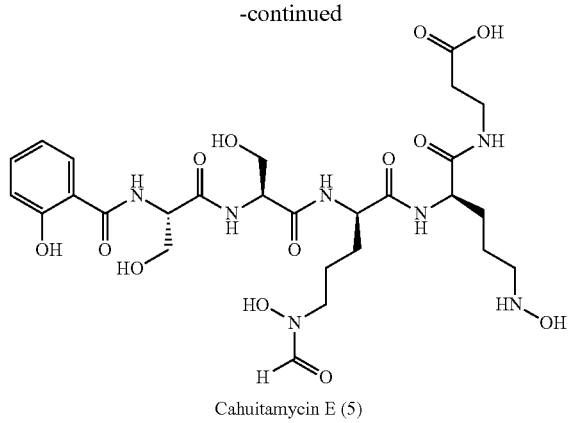

Cahuitamycin E (5)

Cahuitamycin D (4) was isolated from RP-HPLC from crude extract of ΔcahI mutant. The HRESIMS [M+H]⁺ ion peak at m/z 650.2706 provided similar molecular formula as of 3, $C_{28}H_{39}N_7O_{11}$. Extensive 1D and 2D NMR data was acquired for 4, which indicated the expected structural similarity with 3, as per the mutasynthesis hypothesis. The structure showed a similar carbon backbone with a clear difference at the phenyl ring system compared to 3. Cahuitamycin D (4) shows the presence of a singlet at $δ_H$ 7.78 (H-23) with HMBC correlation to $δ_C$ 20.3 (C-25) and $δ_C$ 129.4 (C-24), suggesting methylation at C-24 consistent with the hypothesized incorporation of 5-methyl salicylic acid to the mutant strain DHS334 of *S. gandocaensis*.

Furthermore, during isolation of 4 a concurrent HPLC peak was observed eluting with this natural product. Interestingly, the HRESIMS [M+H]⁺ ion peak at m/z 668.2830 suggested the same backbone with likely additional hydration. Further, 1D and 2D NMR analysis indicated that the new molecule cahuitamycin E (5) share structural similarity on much of the carbon backbone compared to 4. The only plausible difference could be traced at C-5 position where Pip moiety in 4 was substituted with L-N-OH-Orn in 5, suggested based on the COSY relay observed from $δ_H$ 4.33 (H-5) to $δ_H$ 3.45 (H-8) along with absence of any significant HMBC correlation from H-8 to C-9 ($δ_C$ 172.2). The observation was compelling as it indicates that either the cyclization to form Pip moiety is occurring after the insertion of L-N-OH-Orn in 5, or alternatively, the domain is capable of accepting both moieties separately.

The absolute stereochemical configuration of the cahuitamycins D and E (4 and 5) were extrapolated to be the same as cahuitamycins A-C (1-3) based on the very similar chemical shifts observed for all nuclei obtained through detailed 1D and 2D NMR analysis.

Pharmaceutical Compositions and Dosing

The terms "therapeutically effective amount" and "prophylactically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, an improvement in clinical condition, reduction in symptoms, or by any of the assays or clinical diagnostic tests described herein. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

Dosages of the therapeutic can alternately be administered as a dose measured in mg/kg. Contemplated mg/kg doses of the disclosed therapeutics include about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg.

As herein, the compounds described herein may be formulated in pharmaceutical compositions with a pharmaceutically acceptable excipient, carrier, or diluent. The compound or composition comprising the compound is administered by any route that permits treatment of the disease or condition. One route of administration is oral administration. Additionally, the compound or composition comprising the compound may be delivered to a patient using any standard route of administration, including parenterally, such as intravenously, intraperitoneally, intrapulmonary, subcutaneously or intramuscularly, intrathecally, topically, transdermally, rectally, orally, nasally or by inhalation. Slow release formulations may also be prepared from the agents described herein in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

Administration may take the form of single dose administration, or a compound as disclosed herein can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

In an embodiment, the pharmaceutical compositions are formulated with one or more pharmaceutically acceptable excipient, such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders. A pharmaceutical composition can also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

The pharmaceutical compositions described herein are formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate)); and thickening agents (e.g., carbomer, beeswax, hard paraffin or cetyl alcohol). The suspensions may also contain one or more preservatives (e.g., acetic acid, methyl or n-propyl p-hydroxy-benzoate); one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using those suitable dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compounds described herein may be formulated for oral administration in a lipid-based formulation suitable for low solubility compounds. Lipid-based formulations can generally enhance the oral bioavailability of such compounds.

As such, pharmaceutical compositions comprise a therapeutically or prophylactically effective amount of a compound described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In some embodiments, cyclodextrins may be added as aqueous solubility enhancers. Exemplary cyclodextrins include hydroxypropyl, hydroxyethyl, glucosyl, maltosyl and maltotriosyl derivatives of α-, β-, and γ-cyclodextrin. A specific cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the invention in the composition.

Biological Activity Associated with Cahuitamycins

Cahuitamycins A-C(1-3) were next tested for their ability to inhibit biofilm formation of *A. baumannii*. Structurally the molecules resemble a number of previously reported siderophores, including amychelin, oxachelin and gobichelin[18, 22,38] indicating their ability to complex $Fe^{III}$.

Primarily, the static biofilm assay using 1-3 was conducted using crystal violet staining followed by optical density measurements (FIG. 3). The result from this assay showed that 1 was able to inhibit while 2 had no effects on bacterial growth or biofilm formation (FIG. 3). Interestingly, 3 possessed the highest potency with $IC_{50}$ values of 14.5 μM and having a limited effect on growth of *A. baumannii* as desired from a suitable biofilm inhibitor drug candidate (FIG. 3). In addition, when 1 (the most abundant molecule) was tested in iron-complexed form it showed almost no impact on either growth or biofilm formation (FIG. 3). The observation when compared with a known siderophore desferroxamine demonstrated that the siderophore property of the molecule does not impart activity to the cahuitamycins. However, loss of inhibition of biofilm over time can be directly attributed to the metal-complexed cahuitamycins.

Next, the specific stage of inhibition during biofilm formation was probed as well as the extent of inhibition through a flow cell assay. This analysis revealed almost the same number of cells attached to the surface after 1 h of treatment with the bacterial solution. After 6 h of inhibitor supplementation, the flow cells treated with 1 showed only a few micro colonies while the control (no treatment) and desferoxamine showed formation of a robust biofilm. After 24 h of supplementation, the control and desferoxamine biofilm became thicker with the flow cells exposed to 1 showing larger micro colonies and initiation of biofilm formation. In addition, confocal microscope imaging analysis of the *A. baumanii* biofilm was conducted. In this assay, the biofilm was developed on a glass plate and left untreated as a control or treated with only 240 nM of 1 and 3. After treatment with STYO® 9 stain and propidium iodide (PI) the biofilm structure was observed. The images obtained showed a much thinner biofilm and also significantly less total biomass for the glass plates treated with 1 and 3 compared with the control. Furthermore, the glass plate treated with 3 showed a much lower level of total biomass compared to 1 at the same concentration (0.10 μm$^3$ versus 0.18 μm$^3$), confirming 3 to be more potent as a biofilm inhibitor.

Figure 4:
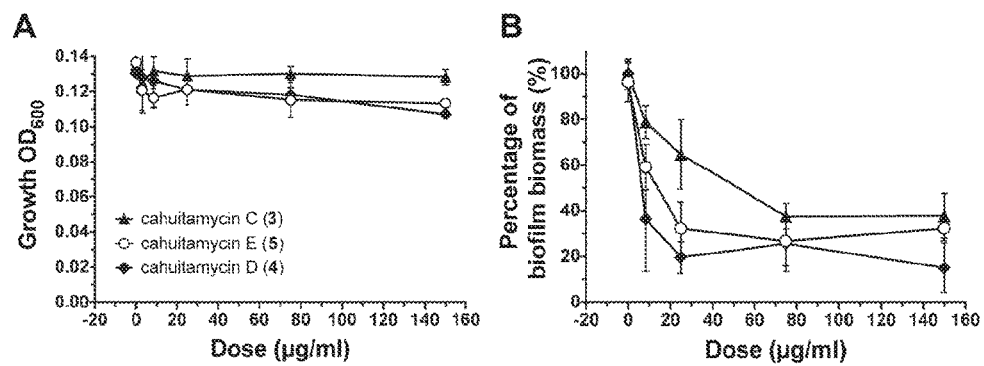
FIG. 4 shows the biological activity of cahuitamycins D (4) and E (5): inhibition of *A. baumannii* growth and biofilm formation by (4) and (5).

As described above the mutasynthetic study on DHS334 led to the isolation of two additional analogs cahuitamycins D-E (4-5). The new molecules were then subjected to static biofilm assay and the result demonstrated that 4 displayed almost twice the potency ($IC_{50}$=8.4 μM) compared to 3, which we earlier considered to be the most active molecule (FIG. 4). Furthermore, cahuitamycin E (5) also displayed significant activity with an $IC_{50}$ of 10.5 μM (FIG. 4). These studies indicate that the key pharmacophore is the 2-hydroxybenzoyl oxazoline group where relatively minor modification can result in an increase (as in case of 3-5) or decrease (as for 2) of anti-biofilm activity.

The emergence of *A. baumannii* as a dangerous nocosomial pathogen has motivated the development of new therapeutic agents to combat its ability to persist in hospitals and the environment. Provided herein is a novel structural class of biofilm inhibitors derived from a marine microbial NPE library. Cahuitamycins A-E inhibit the biofilm formation ability of *A. baumannii* that has been known to be involved in the emergence of an antibiotic resistance phenotype.[1,39-41] The cahuitamycins are capable of binding $Fe^{III}$ but interestingly its apo form shows the highest level of inhibitory activity.

Also provided herein is a bifurcated biosynthetic cluster involved in production of cahuitamycins A-B and cahuitamycins C, separately. The inherently flexible starter unit adenylating enzyme CahI was exploited to produce two additional analogs through incorporation in the engineered ΔcahI strain DHS334. The new cahuitamycin analog D is twice as active as Cahuitamycin C as a biofilm inhibitor. These results establish a unique opportunity for developing and discovering new antibiotics from genetically engineered strains bearing inherent flexibility in pathway initiation processes. More importantly, given the simultaneous decline in antibiotic drug discovery and increase of multidrug resistant bacteria, the cahuitamycins may represent a propitious starting-point for discovery and development of new therapeutics against significant human pathogens.

Thus, provided herein are methods of inhibiting or treating biofilm formation. In some cases, the biofilm results from a bacterial infection. In some cases, the bacteria are selected from *Acinetobacter baumannii, Aeromonas hydrophila, Aeromonas salmonicida, Agrobacterium tumefaciens, Brucella melitensis, Burkholderia cenocepacia, Burkhold-*

*eria mallei, Burkholderia pseudomallei, Burkholderia vietnamiensis, Chromobacterium violaceum, Enterobacter agglomeran, Erwinia carotovora, Erwinia chrysanthemi, Escherichia coli, Nitrosomas europaea, Obesumbacterium proteus, Pantoea agglomerans, Pantoea stewartii, Pseudomonas aureofaciens, Pseudomonas aeruginosa, Pseudomonas fluorescens, Pseudomonas fuscovaginae, Pseudomonas syringae, Ralstonia solanacearum, Rhizobium etli, Rhizobium leguminosarum, Rhodobacter sphaeroides, Serratia liquefaciens, Serratia marcescens, Vibrio anguillarum, Vibrio fischeri, Vibrio parahaemolyticus, Vibrio salmonicida, Xanthomonas campestris, Xenorhabdus nematophilus, Yersinia enterocolitica, Yersinia pestis, Yersinia pseudotuberculosis, Yersinia medievalis, Yersinia ruckeri*, and combinations thereof. In some cases, the bacteria are *Acinetobacter baumannii*. In various cases, the bacteria are contacted with a cahuitamycin compound as disclosed herein. In various cases, the contacting comprises administering to a subject suffering from a bacterial infection. In some cases, the subject is human. In some cases, the subject is an animal.

Further contemplated is administering a second agent to the subject, such as an antibiotic agent. Specific antibiotic agents contemplated include a penicillin, a selexcid, a cephalosporin, a tetracycline, a rifamycin, gentamycin, clindamycin, a fluoroquinolone, a monobactamer, a carbapeneme, a macrolide, a polymyxin, an aminoglycoside, tobramycin, a sulfonamide, a fusidine, a vancomycin, an oxazolidinone, a metronidazole, a corticosteroid, hydrocortisone, triamcinolone, betamethasone, and combinations thereof. The second agent and the cahuitamycin compound can be administered sequentially or at the same time. In some cases, the second agent is administered before the cahuitamycin compound, while in other cases, the second agent is administered after the cahuitamycin compound. In some cases, the second agent and the cahuitamycin compound are co-formulated.

Further provided herein are methods of treating a subject suffering from a disorder associated with biofilm formation comprising administering a cahuitamycin compound as disclosed herein, or a compound as disclosed herein formulated in a composition. Also contemplated is further administering a second agent as disclosed herein, e.g., an antibiotic. In various embodiments, the disorder associated with biofilm formation in the subject is selected from the group consisting of cystic fibrosis, dental caries, periodonitis, otitis media, muscular skeletal infections, necrotizing fasciitis, biliary tract infection, osteomyelitis, bacterial prostatitis, endocarditis, native valve endocarditis, cystic fibrosis pneumonia, meloidosis, or skin lesions associated with bullous impetigo, atopic dermatitis and pemphigus foliaceus or implanted device-related infections. In some embodiments, the condition is a nosocomial infection, including but not limited to, pneumonia or an infection associated with sutures, exit sites, arteriovenous sites, scleral buckles, contact lenses, urinary catheter cystitis, peritoneal dialysis (CAPD) peritonitis, IUDs, endotracheal tubes, Hickman catheters, central venous catheters, mechanical heart valves, vascular grafts, biliary stent blockage, and orthopedic devices.

Also provided is a method of modulating biofilm formation on a surface, the method comprising contacting the surface with a cahuitamycin compound as disclosed herein in an amount effective for disrupt or inhibit biofilm formation on the surface. In one embodiment, the surface is an inanimate surface. Exemplary inanimate surfaces include, but are not limited to, metal, glass, plastic, wood and stone surfaces. In another embodiment, the surface is an animate surface. Exemplary animate surfaces include, but are not limited to, mammalian tissues, mammalian membranes, mammalian skin.

EXAMPLES

General Experimental Procedures. Optical rotation measurements were obtained on a Perkin-Elmer 241 Polarimeter calibrated using a Rudolph Quartz Control Plate Calibration Standard at sodium D line (at +11.502°). UV spectra were obtained on a UV-visible Molecular Devices SpectraMax M5 spectrophotometer using 1 mL cuvettes with 1.0 cm path lengths at room temperature in solvent MeOH. IR spectra were obtained on a Perkin Elmer Spectrum BX FT-IR spectrometer. Spectrophotometric assays were performed on Molecular Devices SpectraMax M5 384 variable wavelength spectrometer. All NMR spectra were acquired on a Varian INOVA 600 MHz and a Varian INOVA 700 MHz spectrometer at the NMR Facility, Department of Chemistry, University of Michigan. High-resolution ESIMS spectra were measured at the University of Michigan core facility in the Department of Chemistry using an Agilent 6520 Q-TOF mass spectrometer equipped with an Agilent 1290 HPLC system. RP-HPLC was performed using Econosil C18 10 μm 22×250 mm column and Agilent ZORBAX RX-C8 5 μm 9.4×250 mm column and a solvent system of MeCN and $H_2O$. The LCMS analysis of HPLC fractions was performed on a Shimadzu 2010 EV APCI spectrometer.

Biological Material. *Streptomyces gandocaensis* (Strain #12620-H2) was isolated from marine sediments collected from Punta Mona Island on Jun., 5, 2007. The procedure for the isolation of actinomycetes from these samples was previously described by Magarvey et al. *Appl. Environ Microbiol.* 2004, 70, 7520. Maintenance and propagation of cultures were performed using standard media and protocols where 500 mg of wet sediment was diluted in 10 mL of sterile water and vortexed for 10 min. Then, 1 mL of this suspension was applied directly to the top of the discontinuous sucrose gradient and centrifuged for 30 minutes at 300×g. 500 μL of the 20%, 30%, and 40% layers were then plated to HVA agar supplemented with 10 μg/mL chlortetracycline, 25 μg/ml cyclohexamide, and 25 μg/ml of nalidixic acid. The plates were then incubated at 28° C. for one month. The colony was picked off the plate and streaked onto ISP2 agar until pure. Seed cultures were grown in 17 mL dual position cap tubes containing 2 mL of ISP2 and grown for 4 days on a rotary shaker at 200 rpm. The seed culture was then poured into a 250 mL baffled flask containing 100 mL of ISP2 and grown for 18 days on a rotary shaker at 200 rpm. The culture was centrifuged at 4000 rpm for 10 min to remove the cells and 2 g of XAD16 resin (Sigma-Aldrich, St. Louis, Mo.) contained within a polypropylene mesh bag was added to the broth and incubated overnight on the rotary shaker. The resin bag was removed and placed into 10 ml of MeOH followed by 10 ml of acetone and 10 ml of ethyl acetate. Each of the three fractions was dried in vacuo and reconstituted to a final concentration of 15 mg/mL in DMSO.

Culture Maintenance and Fermentation. Seed cultures of 100 mL (×5) of ISP2 media (1% malt extract, 0.4% yeast extract, 0.4% dextrose, 3% NaCl) were inoculated with a loopful of vegetative cells from an oatmeal plate (6% oat meal, 1.25% agar, 3% NaCl) culture of *S. gandocaensis* and incubated with shaking (200 rpm) at 28° C. for 5 days. A 25 mL portion of the seed cultures were transferred to a 2.8 L Fernbach flask containing 1.5 L of the ISP2 medium, and the 39L fermentation was carried out on a rotary shaker (200 rpm) at 28° C. for 18 days. After 14-18 days of growth, the cultures were harvested by centrifugation. The resulting cell free broth was subjected to solid phase extraction using 15 g of Amberlite XAD-16. The resin was then separated by filtration and subjected to organic extraction using MeOH: EtOAc (1:1).

Natural Product Extract Library. At the time of screening, the natural product extract (NPE) library at the University of Michigan Center for Chemical Genomics contained ~20,000 extracts. Each extract in the library is derived from marine samples collected from all over the world, including Costa Rica, Panama, and Papua New Guinea. Some of these samples are from isolated microbes (n=19,055) while others were derived from field-collected biomass samples ("macrosamples," n=800). Previous work describes in detail how these extracts are prepared for the library. See Cruz et al., Chem. Biol. 2011 18 1442.

Phylogenetic analysis of 16S rDNA of *Streptomyces gandocaensis*. PCR Amplification, Cloning, and Sequencing of 16S rDNA. Genomic DNA of *Streptomyces gandocaensis* was isolated using the Wizard® Genomic DNA Purification Kit according to the manufacturer's instruction. The 16S rDNA gene was amplified by PCR with the universal primers FC27 (5'-AGAGTTTGATCCTGGCTCAG-3') and RC1492 (5'-TACGGCTACCTTGTTACGACTT-3')[42] using the genomic DNA as a template. The PCR fragments were cloned into pGEM®-T Easy vector (Promega) and the resulting plasmid containing 16S rDNA of *S. gandocaensis* was sequenced using T7 and SP6 primers.

Phylogenetic analysis. Phylogenetic analyses were conducted using GENEIOUS R6 that is available from http://www.geneious.com/ The evolutionary history was inferred using the Neighbor-Joining method. The bootstrap consensus tree inferred from 500 replicates was taken to represent the evolutionary history of the taxa analyzed.

Generation of ribosome engineered mutants of *Streptomyces* sp. 12620-H2. Introduction of mutations conferring resistance to streptomycin. $10^8$-$10^9$ spores of wild-type *S.* sp. 12620-H2 were spread on R2YE agar containing various concentrations of streptomycin, followed by 15 days incubation at 28° C. to allow the development of streptomycin-resistant colonies. Reasonable number (80) of resistant colonies were obtained from the plate containing a high level (10, 50 and 100 m/ml) of streptomycin and grew in ISP2 media with streptomycin for 14 days at 28° C. This step was repeated 4 times to obtain spontaneous streptomycin-resistant mutants. The ability of selected mutants to produce cahuitamyicn was tested by LC/MS analysis.

Amplification and Sequencing of rpsL. It has been known that introduction of streptomycin-resistant mutations results in a point mutation in rpsL gene encoding ribosomal protein S12 in multiple *Streptomyces* species including *Streptomyces lividans* and *Streptomyces coelicolor*. Thus, nine strains, including the parent strain and eight high-yielding recombinants, were selected to determine mutations in the rpsL gene in this study. Genomic DNA of each strain was isolated using the Wizard® Genomic DNA Purification Kit according to the manufacturer's instruction. The rpsL gene was amplified by PCR with primers SR185 and SR186 (Table 3) using the genomic DNA as a template and cloned into pGEM®-T easy vector (promega) and sequenced. Mutations in the wild-type rpsL gene were determined by DNA sequencing.

TABLE 3

Primers

| Primer | Sequence 5' to 3' | Description |
|---|---|---|
| SR144 | GCGCACCGTACGTCTCGAGGAATTCGGGCTCAGTCCGAAGCAG (SEQ ID NO: 8) | Forward and reverse primers for amplification of 5' flanking region of cahI |
| SR145 | TCTGGGGTTCGGGGAGAAACTGCGCAGCGTC (SEQ ID NO: 9) | |
| SR146 | CGGTATCAGGGAACAATCCCGACTCCGCC (SEQ ID NO: 10) | Forward and reverse primers for amplification of 3' flanking region of cahI |
| SR147 | CCGGTGACGTCACCATGGGAAGCTTCGCTGTCGAAGCCGCAGAC (SEQ ID NO: 11) | |
| SR148 | GCAGTTTCTCCCCGAACCCCAGAGTCCC (SEQ ID NO: 12) | Forward and reverse primers for amplification of kanamycin resistance gene |
| SR149 | GGGATTGTTCCCTGATACCGCTCGCCGC (SEQ ID NO: 13) | |
| SR185 | TTGCCGTTCAGCAGCACCTTG (SEQ ID NO: 14) | Primers for amplifying the rpsL |
| SR186 | TTCCAGGTTAGCTGTACACAT (SEQ ID NO: 15) | |
| SR233 | ACTTCTCCCAGACGCACGv (SEQ ID NO: 16) | Primers for verifying the ΔcahI mutant by PCR |
| SR234 | TAACCTAAGTCCAGGGAG (SEQ ID NO: 17) | |
| SR235 | GCCGCGCGGCAGCCATATGCTGATGGGTGGGTG (SEQ ID NO: 18) | Forward and reverse primers for amplification of cahJ |
| SR236 | TCGAGTGCGGCCGCAAGCTTCAGTGGACACCGCCGTC (SEQ ID NO: 19) | |

Isolation and Purification of cahuitamycins A-C(1-3). The organic extracts obtained from the ribosomally modulated strain were concentrated under vacuum to obtain the crude extracts (~350 mg) from 100 mL culture. The crude extract was assayed in the developed in vitro crystal violet at 10 and 1.0 ppm. The bio-active extract was then further purified by RP-HPLC on a gradient of 10-75% ACN and was followed by UV/vis photodiode array detection at 215 nm to yield semi-pure compounds 1 (6.7 mg), 2 (2.4 mg) and 3 (2.9 mg). Compounds were again subjected to re-purification over RP-HPLC on isocratic condition of 35% MeOH (0.1% FA) using C-8 column to get compounds 1 (5.1 mg), 2 (1.1 mg) and 3 (1.6 mg).

Cahuitamycin A (1): bone white, amorphous powder; UV (ACN: $H_2O$) $\lambda_{max}$ 203, 245, 249, 255 and 304 nm; HRES-IMS m/z 636.2679 [M+H]$^+$ (calcd for $C_{27}H_{38}N_7O_{11}$, 636.2629)

Cahuitamycin B (2): bone white, amorphous powder; UV (ACN: $H_2O$) $\lambda_{max}$ 203, 240, 249, 255 and 304 nm; HRES-IMS m/z 654.2759 [M+H]$^+$ (calcd for $C_{28}H_{40}N_7O_{11}$, 654.2735)

Cahuitamycin C (3): bone white, amorphous powder; UV (ACN: $H_2O$) $\lambda_{max}$ 200, 245, 249, 255 and 304 nm; HRES-IMS m/z 650.2804 [M+H]$^+$ (calcd for $C_{27}H_{38}N_7O_{11}$, 650.2786)

Figure 5:
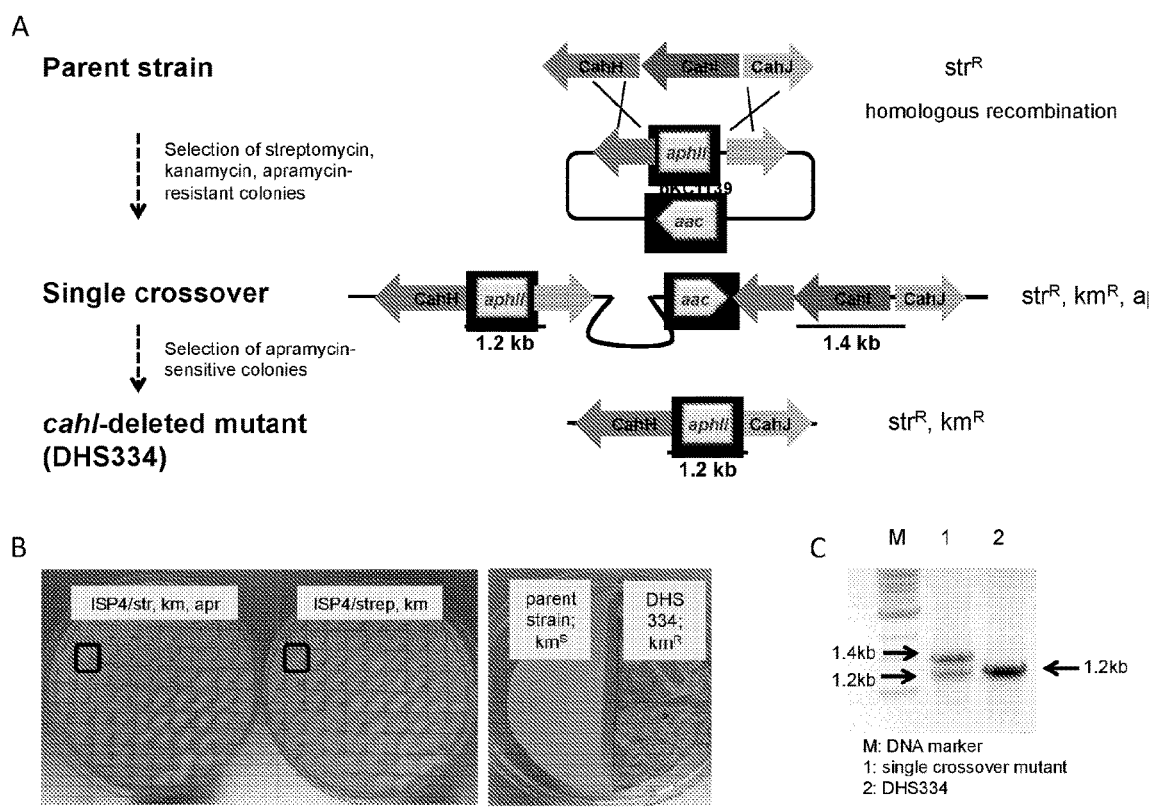
FIG. 5. Replacement of the cahI gene with a kanamycin-resistance gene by homologous recombination. A) A single crossover between pSRP50 and homologous DNA in the genome of the ribosome-engineered *S. gandocaensis* DH287 (streptomycin-resistant as a result of ribosome engineering, i.e., mutating rpsL) gave the pSRP50-integrated strain, and a second crossover generated a cahI-disrupted strain DHS334 (streptomycin- and kanamycin-resistant). B) Selection of streptomycin- and kanamycin-resistant colonies. C) Confirmation of the genotype of the DHS334 by PCR. cahH-siderophore export protein; cahI- salicylate synthase; cahJ-salicylate-AMP ligase; aphII-kanamycin$^r$; aac(3)IV-apramycin$^r$; a mutation in rpsL-streptomycin$^r$.

Generation of cahI deletion mutant. Construction of deletion plasmid. A knock-out plasmid based on pKC1139 (containing the apramycin resistance gene aac(3)IV) was constructed by amplifying the kanamycin resistance gene (aphII) as a selection marker from plasmid pYJ276, and left- and right-flanking regions of the cahI gene using the genomic DNA of *S. gandocaensis* as a template with KOD xtreme polymerase (Novagen). The primer pairs SR144-SR145, SR146-SR147, and SR148-SR149 (Table 3) were designed for amplification of the left-flanking fragment of the cahI gene, the right-flanking fragment of the cahI gene and the selection marker, respectively. DNA assembly was performed using the Gibson assembly master mix (New England Biolabs) according to the manufacturer's instructions. Briefly, the amplified PCR products of the DNA region containing the kanamycin resistance gene and the DNA fragments containing the two flanking regions of the cahI gene, the pKC1139 vector linearized by EcoRI and HindIII digestion, and the Gibson assembly master mix were incubated at 50° C. for 2 hr. Following incubation, the samples were transformed into E. coli DH5a and isolated with application of appropriate antibiotic selection. Restriction digestion and sequencing verified the isolated plasmid designated pSRP50 (FIG. 5A).

Transformation of S. gandocaensis with the deletion plasmid. The plasmid pSRP50 was passaged through methylation-deficient E. coli ET12567 and then introduced into the S. gandocaensis by protoplasts-based transformation. The target region of the cahI gene was then disrupted by an insertional inactivation via double crossover homologous recombination (FIG. 5A). A single crossover product was selected by cultivation of apramycin and kanamycin-resistant transconjugants at 37° C. (the non-permissive temperature for the pSG5-based replicon) in the presence of two antibiotics. The transformants resulting from single crossover were grown through one round of propagation in the absence of apramycin to allow for the second crossover. The desired double crossover mutant ΔcahI was selected by its kanamycin-resistant and apramycin-sensitive phenotype (FIG. 5B) and verified by PCR (FIG. 5C) using the primer pair SR233-SR234 (Table 3). The resulting cahI-deletion mutant of S. gandocaensis was designated DHS334.

Chemical complementation of cahI deletion mutant of DHS334 and mutasynthesis of cahuitamyin analogs. Mutant strain of DHS334 was first precultured in 3 ml R2YE liquid medium for 15 days at 28° C. and then 3 ml of the seed culture was used to inoculate 100 ml of the same medium, followed by cultivation for 15 days at 28° C. Salicylic acid and a series of substituted benzoic acid substrates, 2-hydroxybenzoic acid, 2,3-dihydroxybenzoic acid, 2,4-dihydroxybenzoic acid, 2-fluorobenzoic acid, 2-hydoxy-5-methylbenzoic acid (5-methylsalicylic acid), 2-hydoxy-6-methylbenzoic acid (6-methylsalicylic acid) were added every alternate day to separate 100 ml-cultures of DHS334 at a final concentration of 500 µM for 15 days. The products were first extracted using Amberlite XAD-16. The resin was separated and subjected to organic extraction using MeOH:EtOAc (1:1) for LC-MS analysis as described above.

The substrate fed crude extract was then further purified by RP-HPLC on a gradient of 10-75% ACN and was followed by UV/vis photodiode array detection at 215 nm to yield semi-pure compounds 4 (2.4 mg) and 5 (2.6 mg). Compounds were again subjected to re-purification over RP-HPLC on isocratic condition of 35% MeOH (0.1% FA) using C-8 column to get compounds 4 (1.1 mg) and 5 (1.3 mg).

Cahuitamycin D (4): amorphous powder; UV (ACN:H$_2$O) $\lambda_{max}$ 203, 240, 249, 255 and 304 nm; HRESIMS m/z 650.2706 [M+H]$^+$ (calcd for C$_{28}$H$_{40}$N$_7$O$_{11}$, 650.2786)

Cahuitamycin E (5): amorphous powder; UV (ACN:H$_2$O) $\lambda_{max}$ 200, 245, 249, 255 and 304 nm; HRESIMS m/z 668.2830 [M+H]$^+$ (calcd for C$_{28}$H$_{42}$N$_7$O$_{12}$, 668.2891)

Determination of pFeIII for amychelin. Determination of pFe$^{III}$ for cahuitamycins was carried out as reported by Abergel et al. J. Am. Chem. Soc. 2007 130 2124, essentially without modifications. Briefly, purified Fe-cahuitamycins, prepared as described above, was dissolved in Hepes buffer (10 mM Hepes, 0.1 M KCl, pH 7.4) and five different concentration ranges of ETDA were added from EDTA stock solutions also prepared in HEPES buffer. Each reaction consisted of a total volume of 0.25 mL, a final concentration of 0.1 mM Fe-cahuitamycins and a range of 5-fold-8000-fold EDTA (relative to Fe-cahuitamycins) in Hepes buffer. The reaction was allowed to equilibrate at room temperature for at least 24 h, and UV-visible spectra were subsequently recorded. The composite spectra contain contributions from both Fe-EDTA and Fe-cahuitamycins. The ε of both species as a function of λ, were determined in Hepes buffer and used to deconvolute the spectra. The contribution of Fe-cahuitamycins was subtracted from the composite spectra using the 435 nm absorption band and the ε of both Fe-cahuitamycins and Fe-EDTA were used to quantify the proportion of each species in solution. Concentrations of apo-EDTA and apo-cahuitamycins were calculated by subtracting [Fe-EDTA] (or [Fe-cahuitamycins]) from total initial EDTA (or Fe cahuitamycins). The log [EDTA]/[cahuitamycins] was plotted against log [Fe-EDTA]/[Fe-cahuitamycins] and the data were fit to the following equation, which has been derived by Abergel et al., J. Am. Chem. Soc., 2007 130 2124. log ([Fe-EDTA]/[Fe-cahuitamycin])=log ([EDTA]/[cahuitamycin])+ΔpFe$^{III}$ Assay Development and High-Throughput Screening A static biofilm assay was developed from a previously reported method.[10] The biofilm assay measures the adhesion of bacteria to the surface of polystyrene 384 well microtiter plates. Adherent cells are detected by staining with Crystal Violet and subsequent washing to remove nonadherent planktonic cells. Inhibitors of biofilm formation prevent the bacteria from adhering to the surface of the microtiter plate and reduce the amount of Crystal Violet retained after washing. Assay quantification was performed by OD$_{600}$ absorbance measurement of the Crystal Violet stained biofilm. The assay was optimized for plate surface treatment, time, temperature, media, media concentration, Crystal Violet concentration, wash method, inhibitor sensitivity, and culture inoculum preparation.

The A. baumannii test strain (ATCC 17978) was maintained as a frozen stock at −80° C. in 20% glycerol. On the morning of the assay, 5 ml of Mueller Hinton II cation adjusted media (Becton Dickinson cat. 212322) was inoculated and grown at 37° C., 180 rpm shaking for 4-6 h. The culture was then diluted 1:50 and incubated an additional 2 h. The resulting cells were washed four times by centrifugation and resuspension of the pellet in media was performed to remove any metabolites or cell signaling factors. The assay inoculum was prepared by diluting the cells to 0.008 OD$_{600}$ in 10% Mueller Hinton II cation adjusted media (diluted in 18 ohm deionized water). The assay plates (Corning cat. 3680, 384 well non-treated polystyrene) were prepared by dispensing 20 µl of 10% Mueller Hinton II cation adjusted media into columns 1-22 using a Multidrop Combi dispenser (ThermoFisher). The natural product extract samples were added as 0.2 µl of 15 mg/ml stocks in DMSO using a Biomek FX high density pintool (Beckman Coulter). Column 1 and 2 contained DMSO without natural product extracts and served as the negative control. The positive control was added to column 23 and 24 as 20 µl of 40 µM Baicalein (Sigma-Aldrich cat. 11712). The bacterial cells were added to the entire plate in 20 µl of the prepared inoculum using a Multidrop Combi dispenser (ThermoFisher). The resulting assay contained 40 µl of 10% Mueller Hinton II cation adjusted media with 0.004 OD600 bacterial cells, 0.5% DMSO, and 75 µg/ml natural product extract. The assay plates were incubated at 30° C. for 20 h, stationary, in a humidified incubator. The biofilm was stained by adding 10 µl of filtered 1% Crystal Violet and incubating for 30 minutes at room temperature. Excess Crystal Violet and nonadherent planktonic cells were removed by washing three times with 150 µl of PBS using an ELX405 plate washer (Biotek). The wash program used a low velocity dispense rate and an aspiration height of 3.8 mm; about 10 µl of PBS remained in the well after washing. The Crystal Violet stained biofilm was solubilized by the addition of 50 µl of 100% ethanol and allowed to develop overnight. Quantification was performed by measuring the $OD_{600}$ absorbance using a Pherastar plate reader (BMG).

Biofilms were formed by *A. baumannii* ATCC 17978 in flow chambers at room temperature. Images were taken at 1 h, 6 h and 24 h (by using a 60× lens) after inoculation. A flow cell biofilm was achieved by using a flow cell chamber (ACCFL0001, Life Science Incorporated, Greensboro, N.C.). Briefly, overnight cultures of *A. baumannii* ATCC 17978 grown in MHII broth at 37° C. were diluted 100 fold with fresh MHII broth. 1 ml of dilution was injected into a flow cell chamber and allowed to settle one hour for attaching of bacteria followed by initiation media flow. Flow media was 10% MHII broth (control), or 10% MHII broth with 7.5 µg/ml of desferoxamine, or MHII broth with 7.5 µg/ml of cahuitamycins A. The flow rate was 4 ml/hr. Micrographs of the biofilm were acquired at 1 h, 6 h and 24 h by using an Olympus IX70 microscope with 60× lens

REFERENCES (1) Dijkshoorn, et al. *Nature reviews. Microbiology* 2007, 5, 939.
(2) Andersson, et al. *FEMS microbiology reviews* 2011, 35, 901.
(3) Livermore. *The Journal of antimicrobial chemotherapy* 2011, 66, 1941.
(4) Fischbach, et al. *Science* 2009, 325, 1089.
(5) Tripathi, et al. *J. Am. Chem. Soc.* 2014, 136(4), 1579.
(6) Sunenshine, et al. *Emerg Infect Dis* 2007, 13, 97.
(7) Chang Shan-Chwen; et al. *Diagnos Microbiol Infect Dis.* 1995, 23, 105.
(8) Davies, D. *Nature reviews. Drug discovery* 2003, 2, 114.
(9) Magarvey, et al. *Applied and environmental microbiology* 2004, 70(12), 7520.
(10) Newman, et al. *J. Nat. Prod.* 2012, 75, 311.
(11) Montaser, et al. *Future Med. Chem.* 2011, 3, 1475.
(12) Ochi, et al. *ADVANCES IN APPLIED MICROBIOLOGY* 2004, 56, 155.
(13) Fuji, et al. *I. Anal. Chem.* 1997, 69, 3346.
(14) Marfey. *Carlsberg Res. Commun.* 1984, 49, 591.
(15) Abergel, et al. *J. Am. Chem. Soc.* 2008, 130, 2124.
(16) Smith, et al. *Critical Stability Constants* New York, 1977; Vol. 1-4.
(17) Blin, et al. *In Nuc. Acids Res* 2013; Vol. 41, p W204.
(18) Seyedsayamdost, et al. *J. Am. Chem. Soc.* 2011; Vol. 133, p 11434.
(19) Harrison, et al. *J. Bacteriol.* 2006, 188, 6081.
(20) Schneiker, et al. *Nat. Biotechnol.* 2007, 25, 1281.
(21) Bachmann, et al. *In Meth. Enzymol.* 2009; Vol. 458, p 181.
(22) Chen, et al. *Med. Chem. Commun.* 2013, 4, 233.
(23) von Döhren, et al. *In Chem. Rev.* 1997; Vol. 97, p 2675.
(24) Marahiel, et al, *Chem. Rev.* 1997; Vol. 97, p 2651.
(25) Tao, et al. *Organic Letters* 2003, 5, 1213.
(26) Neumann, et al. *Chembiochem* 2012, 13, 972.
(27) Broberg, et al., *J. Nat. Prod.* 2006; Vol. 69, p 97.
(28) Bevan, et al. *J Chem Soc C: Organic* 1971, 514.
(29) Fehr, et al., *J. Antibiot.* 1999; Vol. 52, p 474.
(30) Umezawa, et al. *J Chem Soc, Perkin Transactions 1* 2001.
(31) Umezawa, et al. *J Org Chem* 1999, 64 (9), 3034.
(32) Arroyo, et al. *J Am Chem Soc* 1976, 845.
(33) Zhao, et al. *Cell Research* 2010, 20, 1096.
(34) Lautru, et al *Nat. Chem. Biol.* 2005; Vol. 1, p 265.
(35) Herbst, et al *J Biol Chem* 2013; Vol. 288, p 1991.
(36) Ling, et al., *J. Am. Chem. Soc.* 2010; Vol. 132, p 12534.
(37) Daum, et al., *ChemBioChem* 2009; Vol. 10, p 1073.
(38) Sontag, et al. *J Antibiotics* 2006, 59 (10), 659.
(39) Gaisser, et al. *J. Bacteriol.* 1997, 179, 6271.
(40) Shao, et al. *Biochem. Biophys. Res. Commun.* 2006, 345, 133.
(41) Rao, et al. *Ind. J. Med. Micro.* 2008, 26, 333.
(1) Dijkshoorn, et al. *Nature reviews. Microbiology* 2007, 5, 939.
(2) Andersson, et al. *FEMS microbiology reviews* 2011, 35, 901.
(3) Livermore. *The Journal of antimicrobial chemotherapy* 2011, 66, 1941.
(4) Fischbach, et al. *Science* 2009, 325, 1089.
(5) Tripathi, et al. *J. Am. Chem. Soc.* 2014, 136(4), 1579.
(6) Sunenshine, et al. *Emerg Infect Dis* 2007, 13, 97.
(7) Chang Shan-Chwen; et al. *Diagnos Microbiol Infect Dis.* 1995, 23, 105.
(8) Davies, D. *Nature reviews. Drug discovery* 2003, 2, 114.
(9) Magarvey, et al. *Applied and environmental microbiology* 2004, 70(12), 7520.
(10) Newman, et al. *J. Nat. Prod.* 2012, 75, 311.
(11) Montaser, et al. *Future Med. Chem.* 2011, 3, 1475.
(12) Ochi, et al. *ADVANCES IN APPLIED MICROBIOLOGY* 2004, 56, 155.
(13) Fuji, et al. *I. Anal. Chem.* 1997, 69, 3346.
(14) Marfey. *Carlsberg Res. Commun.* 1984, 49, 591.
(15) Abergel, et al. *J. Am. Chem. Soc.* 2008, 130, 2124.
(16) Smith, et al. *Critical Stability Constants* New York, 1977; Vol. 1-4.
(17) Blin, et al. *In Nuc. Acids Res* 2013; Vol. 41, p W204.
(18) Seyedsayamdost, et al. *J. Am. Chem. Soc.* 2011; Vol. 133, p 11434.
(19) Harrison, et al. *J. Bacteriol.* 2006, 188, 6081.
(20) Schneiker, et al. *Nat. Biotechnol.* 2007, 25, 1281.
(21) Bachmann, et al. *In Meth. Enzymol.* 2009; Vol. 458, p 181.
(22) Chen, et al. *Med. Chem. Commun.* 2013, 4, 233.
(23) von Döhren, et al. *In Chem. Rev.* 1997; Vol. 97, p 2675.
(24) Marahiel, et al, *Chem. Rev.* 1997; Vol. 97, p 2651.
(25) Tao, et al. *Organic Letters* 2003, 5, 1213.
(26) Neumann, et al. *Chembiochem* 2012, 13, 972.
(27) Broberg, et al., *J. Nat. Prod.* 2006; Vol. 69, p 97.
(28) Bevan, et al. *J Chem Soc C: Organic* 1971, 514.
(29) Fehr, et al., *J. Antibiot.* 1999; Vol. 52, p 474.
(30) Umezawa, et al. *J Chem Soc, Perkin Transactions 1* 2001.
(31) Umezawa, et al. *J Org Chem* 1999, 64 (9), 3034.
(32) Arroyo, et al. *J Am Chem Soc* 1976, 845.
(33) Zhao, et al. *Cell Research* 2010, 20, 1096.
(34) Lautru, et al *Nat. Chem. Biol.* 2005; Vol. 1, p 265.
(35) Herbst, et al *J Biol Chem* 2013; Vol. 288, p 1991.
(36) Ling, et al., *J. Am. Chem. Soc.* 2010; Vol. 132, p 12534.
(37) Daum, et al., *ChemBioChem* 2009; Vol. 10, p 1073.
(38) Sontag, et al. *J Antibiotics* 2006, 59 (10), 659.
(39) Gaisser, et al. *J. Bacteriol.* 1997, 179, 6271.
(40) Shao, et al. *Biochem. Biophys. Res. Commun.* 2006, 345, 133.
(41) Rao, et al. *Ind. J. Med. Micro.* 2008, 26, 333.
(42) Rainey, et al. *Int. J. Syst. Bacteriol.* 1996, 46, 1088.

What is claimed is:

1. A compound having a structure:

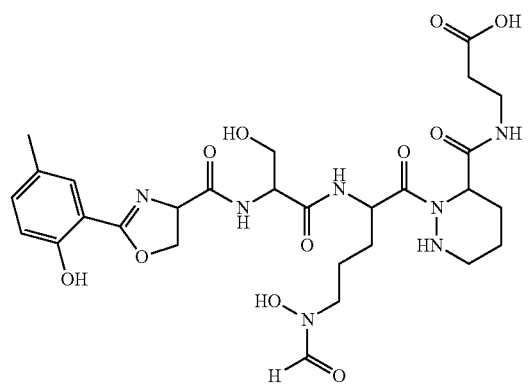

or

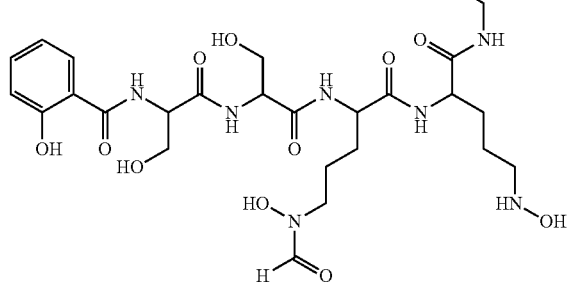

or a pharmaceutically acceptable salt thereof.

2. The compound of claim 1 having a structure

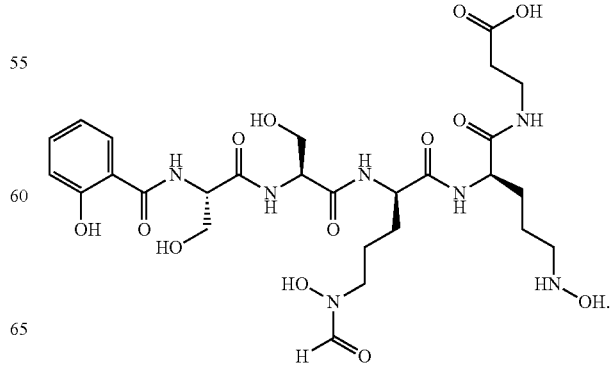

3. The compound of claim 1 having a structure

4. A composition comprising (a) a cahuitamycin compound or pharmaceutically acceptable salt thereof and (b) a pharmaceutically acceptable carrier, wherein the cahuitamycin compound has a structure selected from:

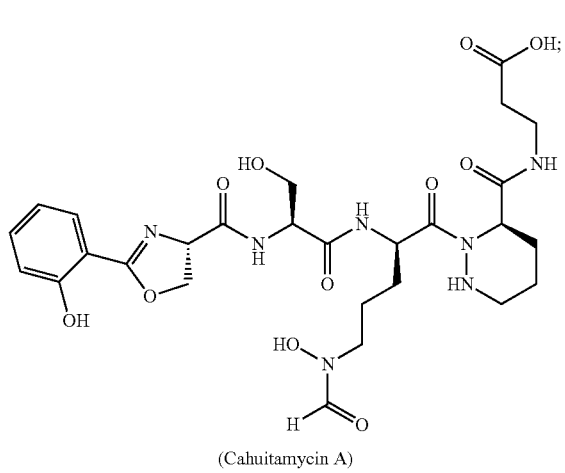

(Cahuitamycin A)

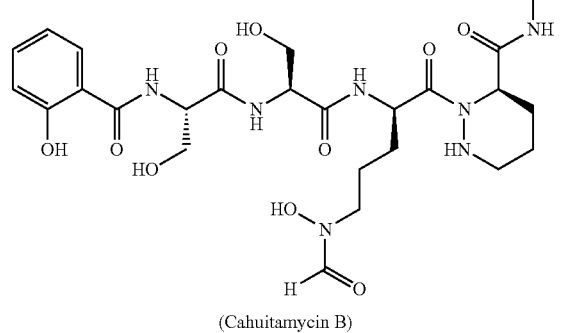

(Cahuitamycin B)

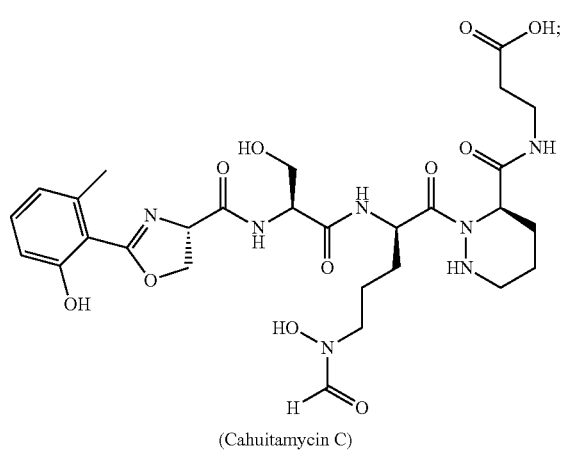

(Cahuitamycin C)

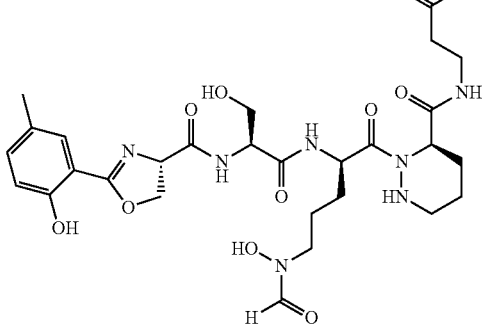

(Cahuitamycin D)

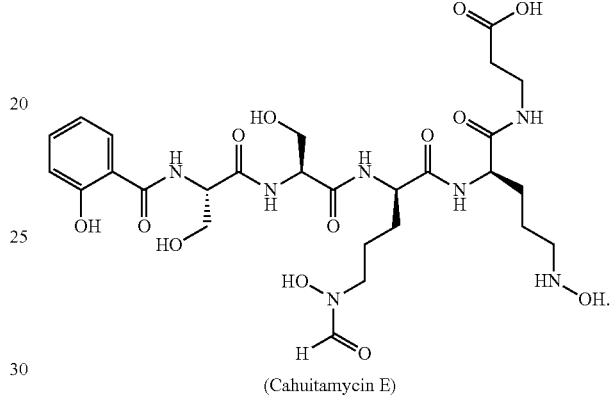

(Cahuitamycin E)

5. A method of inhibiting biofilm formation comprising contacting a bacterium capable for forming a biofilm with the composition of claim 4 in an amount sufficient to inhibit the biofilm formation.

6. The method of claim 5, wherein the biofilm is formed by a bacterium that is selected from the group consisting of: *Acinetobacter baumannii, Aeromonas hydrophila, Aeromonas salmonicida, Agrobacterium tumefaciens, Brucella melitensis, Burkholderia cenocepacia, Burkholderia mallei, Burkholderia pseudomallei, Burkholderia vietnamiensis, Chromobacterium violaceum, Enterobacter agglomeran, Erwinia carotovora, Erwinia chrysanthemi, Escherichia coli, Nitrosomas europaea, Obesumbacterium proteus, Pantoea agglomerans, Pantoea stewartii, Pseudomonas aureofaciens, Pseudomonas aeruginosa, Pseudomonas fluorescens, Pseudomonas fuscovaginae, Pseudomonas syringae, Ralstonia solanacearum, Rhizobium etli, Rhizobium leguminosarum, Rhodobacter sphaeroides, Serratia liquefaciens, Serratia marcescens, Vibrio anguillarum, Vibrio fischeri, Vibrio parahaemolyticus, Vibrio salmonicida, Xanthomonas campestris, Xenorhabdus nematophilus, Yersinia enterocolitica, Yersinia pestis, Yersinia pseudotuberculosis, Yersinia medievalis, Yersinia ruckeri*, and a combination thereof.

7. A method of treating a condition due to biofilm formation in a subject in need thereof comprising administering the composition of claim 4 to the subject.

8. The method of claim 7, wherein the condition is selected from the group consisting of: cystic fibrosis, dental caries, periodonitis, otitis media, a muscular skeletal infection, pneumonia, necrotizing fasciitis, biliary tract infection, osteomyelitis, bacterial prostatitis, endocarditis, native valve endocarditis, cystic fibrosis pneumonia, meloidosis, a skin lesion associated with bullous impetigo, atopic dermatitis, pemphigus foliaceus, and an implanted device-related infection.

9. The method of claim 7, further comprising administering a second therapeutic to the subject.

10. The method of claim 9, wherein the second therapeutic comprises an antibiotic.

11. A method of producing a cahuitamycin compound comprising
   (a) culturing *Streptomyces gandocaensis*
      (i) in the presence of streptomycin to select for a mutated ribosomal protein, thereby generating a mutated *S. gandocaensis*,
      (ii) under conditions wherein the activity of salicylate synthase is inhibited;
      (iii) under conditions wherein the activity of 6-methylsalicylic acid synthase is inhibited;
      (iv) in the presence of 2-hydroxy-5-methylbenzoic acid or 2-hydroxybenzoic acid and the mutant is *Streptomyces gandocaensis* lacking salicylate synthase activity; and
   (b) obtaining the cahuitamycin compound from the culture.

12. The method of claim 11, wherein the *Streptomyces gandocaensis* comprises a rpsL gene mutation, or a cahI mutation.

13. The method of claim 11, wherein the *S. gandocaensis* is cultured in the present of streptomycin and the cahuitamycin compound is cahuitamycin D, cahuitamycin E or a mixture of cahuitamycins D and E.

14. The method of claim 11, wherein the production of cahuitamycin A, cahuitamycin B, or a mixture of cahuitamycin A and B is increased due to culturing the *Streptomyces gandocaensis* under conditions wherein the activity of 6-methylsalicylic acid synthase is inhibited.

15. The method of claim 11, comprising
   culturing the *Streptomyces gandocaensis* in the presence of 2-hydroxy-5-methylbenzoic acid to form cahuitamycin D.

16. The method of claim 11, comprising culturing the *Streptomyces gandocaensis* in the presence of 2-hydroxybenzoic acid to form cahuitamycin E.

17. The method of claim 15, further comprising isolating the cahuitamycin D.

18. The method of claim 17, wherein the isolating comprises subjecting crude cahuitamycin D to extraction, chromatography, or both.

19. The method of claim 18, wherein the extraction comprises contacting with an adsorbant resin, such as a styrene-divinylbenzene matrix.

20. The method of claim 18, wherein the chromatography is fractionation, high performance liquid chromatography, reverse phase liquid chromatography or a combination thereof.

* * * * *

SEQUENCE LISTING

<160> NUMBER OF SEQ ID NOS: 19

<210> SEQ ID NO 1
<211> LENGTH: 324
<212> TYPE: DNA
<213> ORGANISM: Streptomyces
<220> FEATURE:
<221> NAME/KEY: misc_feature
<222> LOCATION: (91)..(91)
<223> OTHER INFORMATION: A to G
<220> FEATURE:
<221> NAME/KEY: misc_feature
<222> LOCATION: (175)..(175)
<223> OTHER INFORMATION: A to G
<220> FEATURE:
<221> NAME/KEY: misc_feature
<222> LOCATION: (232)..(232)
<223> OTHER INFORMATION: C to T

<400> SEQUENCE: 1
gacaaggtcg agaagaacaa gacgcccgca ctcgagggtt cgccccagcg ccgtggcgtc    60
tgcacgcgtg tgttcacgac caccccgaag aagccgaact cggccctgcg taaggtcgcg   120
cgtgtgcgtc tgaccagcgg catcgaggtc accgcttaca ttccgggtga gggacacaac   180
ctgcaggagc actccatcgt gctcgtgcgc ggcggccgtg tgaaggacct gccgggtgtt   240
cgctacaaga tcatccgagg ctccctcgac acccagggtg tcaagaaccg caagcaggcc   300
cgcagccgtt acggcgccaa gaag                                          324

<210> SEQ ID NO 2
<211> LENGTH: 108
<212> TYPE: PRT
<213> ORGANISM: Streptomyces
<220> FEATURE:
<221> NAME/KEY: MISC_FEATURE
<222> LOCATION: (30)..(30)
<223> OTHER INFORMATION: Lys to Arg
<220> FEATURE:
<221> NAME/KEY: MISC_FEATURE
<222> LOCATION: (69)..(69)
<223> OTHER INFORMATION: Val to Met
<220> FEATURE:
<221> NAME/KEY: MISC_FEATURE
<222> LOCATION: (78)..(78)
<223> OTHER INFORMATION: Pro to Thr

<400> SEQUENCE: 2

Asp Lys Val Glu Lys Asn Lys Thr Pro Ala Leu Glu Gly Ser Pro Gln
1               5                   10                  15

Arg Arg Gly Val Cys Thr Arg Val Phe Thr Thr Pro Lys Lys Pro
            20                  25                  30

Asn Ser Ala Leu Arg Lys Val Ala Arg Val Arg Leu Thr Ser Gly Ile
        35                  40                  45

Glu Val Thr Ala Tyr Ile Pro Gly Glu Gly His Asn Leu Gln Glu His
    50                  55                  60

Ser Ile Val Leu Val Arg Gly Gly Arg Val Lys Asp Leu Pro Gly Val
65                  70                  75                  80

Arg Tyr Lys Ile Ile Arg Gly Ser Leu Asp Thr Gln Gly Val Lys Asn
                85                  90                  95

Arg Lys Gln Ala Arg Ser Arg Tyr Gly Ala Lys Lys
            100                 105

<210> SEQ ID NO 3
<211> LENGTH: 10
<212> TYPE: PRT

```
<213> ORGANISM: Streptomyces gandocaensis

<400> SEQUENCE: 3

Asp Leu Tyr Asn Leu Gly Leu Ile His Lys
1               5                   10

<210> SEQ ID NO 4
<211> LENGTH: 10
<212> TYPE: PRT
<213> ORGANISM: Streptomyces gandocaensis

<400> SEQUENCE: 4

Asp Val Trp His Val Ser Leu Val Asp Lys
1               5                   10

<210> SEQ ID NO 5
<211> LENGTH: 10
<212> TYPE: PRT
<213> ORGANISM: Streptomyces gandocaensis

<400> SEQUENCE: 5

Asp Ile Asn Tyr Trp Gly Gly Ile Gly Lys
1               5                   10

<210> SEQ ID NO 6
<211> LENGTH: 10
<212> TYPE: PRT
<213> ORGANISM: Streptomyces gandocaensis

<400> SEQUENCE: 6

Asp Ala Trp Glu Gly Gly Leu Val Asp Lys
1               5                   10

<210> SEQ ID NO 7
<211> LENGTH: 10
<212> TYPE: PRT
<213> ORGANISM: Streptomyces gandocaensis

<400> SEQUENCE: 7

Ile Asp Val Thr Ile Ser Leu Ala Asp Lys
1               5                   10

<210> SEQ ID NO 8
<211> LENGTH: 43
<212> TYPE: DNA
<213> ORGANISM: Artificial sequence
<220> FEATURE:
<223> OTHER INFORMATION: Synthetic primer

<400> SEQUENCE: 8
gcgcaccgta cgtctcgagg aattcgggct cagtccgaag cag            43

<210> SEQ ID NO 9
<211> LENGTH: 31
<212> TYPE: DNA
<213> ORGANISM: Artificial sequence
<220> FEATURE:
<223> OTHER INFORMATION: Synthetic primer

<400> SEQUENCE: 9
tctggggttc ggggagaaac tgcgcagcgt c                         31

<210> SEQ ID NO 10
<211> LENGTH: 29
<212> TYPE: DNA
```

<213> ORGANISM: Artificial sequence
<220> FEATURE:
<223> OTHER INFORMATION: Synthetic primer

<400> SEQUENCE: 10
cggtatcagg gaacaatccc gactccgcc                               29

<210> SEQ ID NO 11
<211> LENGTH: 44
<212> TYPE: DNA
<213> ORGANISM: Artificial sequence
<220> FEATURE:
<223> OTHER INFORMATION: Synthetic primer

<400> SEQUENCE: 11
ccggtgacgt caccatggga agcttcgctg tcgaagccgc agac              44

<210> SEQ ID NO 12
<211> LENGTH: 28
<212> TYPE: DNA
<213> ORGANISM: Artificial sequence
<220> FEATURE:
<223> OTHER INFORMATION: Synthetic primer

<400> SEQUENCE: 12
gcagtttctc cccgaacccc agagtccc                                28

<210> SEQ ID NO 13
<211> LENGTH: 28
<212> TYPE: DNA
<213> ORGANISM: Artificial sequence
<220> FEATURE:
<223> OTHER INFORMATION: Synthetic primer

<400> SEQUENCE: 13
gggattgttc cctgataccg ctcgccgc                                28

<210> SEQ ID NO 14
<211> LENGTH: 21
<212> TYPE: DNA
<213> ORGANISM: Artificial sequence
<220> FEATURE:
<223> OTHER INFORMATION: Synthetic primer

<400> SEQUENCE: 14
ttgccgttca gcagcacctt g                                       21

<210> SEQ ID NO 15
<211> LENGTH: 21
<212> TYPE: DNA
<213> ORGANISM: Artificial sequence
<220> FEATURE:
<223> OTHER INFORMATION: Synthetic primer

<400> SEQUENCE: 15
ttccaggtta gctgtacaca t                                       21

<210> SEQ ID NO 16
<211> LENGTH: 18
<212> TYPE: DNA
<213> ORGANISM: Artificial sequence
<220> FEATURE:
<223> OTHER INFORMATION: Synthetic primer

<400> SEQUENCE: 16
acttctccca gacgcacg                                           18

```
<210> SEQ ID NO 17
<211> LENGTH: 18
<212> TYPE: DNA
<213> ORGANISM: Artificial sequence
<220> FEATURE:
<223> OTHER INFORMATION: Synthetic primer

<400> SEQUENCE: 17
taacctaagt ccagggag                                                 18

<210> SEQ ID NO 18
<211> LENGTH: 34
<212> TYPE: DNA
<213> ORGANISM: Artificial sequence
<220> FEATURE:
<223> OTHER INFORMATION: Synthetic primer

<400> SEQUENCE: 18
gccgcgcggc agccatatgc tcgatgggtg ggtg                                34

<210> SEQ ID NO 19
<211> LENGTH: 37
<212> TYPE: DNA
<213> ORGANISM: Artificial sequence
<220> FEATURE:
<223> OTHER INFORMATION: Synthetic primer

<400> SEQUENCE: 19
tcgagtgcgg ccgcaagctt cagtggacac cgccgtc                             37
```